(12) United States Patent
Xu

(10) Patent No.: US 10,240,994 B1
(45) Date of Patent: Mar. 26, 2019

(54) WIRELESS CYLINDRICAL SHELL PASSIVE LC SENSOR

(71) Applicant: W. L. Gore & Associates, Inc., Newark, DE (US)

(72) Inventor: Minghua Xu, Hockessin, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 18 days.

(21) Appl. No.: 15/688,434

(22) Filed: Aug. 28, 2017

Related U.S. Application Data

(60) Provisional application No. 62/380,206, filed on Aug. 26, 2016.

(51) Int. Cl.
| | |
|---|---|
| *G01L 9/12* | (2006.01) |
| *G01L 9/00* | (2006.01) |
| *A61B 5/02* | (2006.01) |
| *A61B 5/00* | (2006.01) |
| *G01L 19/06* | (2006.01) |

(52) U.S. Cl.
CPC .............. *G01L 9/12* (2013.01); *A61B 5/0031* (2013.01); *A61B 5/02014* (2013.01); *G01L 9/0072* (2013.01); *G01L 19/069* (2013.01); *A61B 2562/0247* (2013.01)

(58) Field of Classification Search
CPC ....... G01L 9/12; G01L 19/069; G01L 9/0072; A61B 5/02014; A61B 2562/0247; A61B 5/0031
See application file for complete search history.

(56) References Cited

U.S. PATENT DOCUMENTS

| | | | |
|---|---|---|---|
| 3,228,030 A | 1/1966 | Moore | |
| 4,206,762 A | 6/1980 | Cosman | |
| 5,144,098 A * | 9/1992 | VanDeusen | ............ H01B 11/10 174/102 SC |
| 5,480,415 A | 1/1996 | Cox et al. | |
| 5,967,986 A * | 10/1999 | Cimochowski | ...... A61B 5/0031 600/454 |
| 6,015,386 A | 1/2000 | Kensey | |
| 6,206,835 B1 | 3/2001 | Spillman et al. | |
| 6,231,516 B1 * | 5/2001 | Keilman | ............... A61B 5/0031 600/481 |
| 6,585,763 B1 * | 7/2003 | Keilman | ............... A61B 5/0031 604/891.1 |
| 6,855,115 B2 | 2/2005 | Cardiomems | |
| 7,146,861 B1 | 12/2006 | Cook et al. | |
| 7,181,975 B1 | 2/2007 | Bradley | |
| 7,191,013 B1 | 3/2007 | Miranda et al. | |
| 7,245,117 B1 | 7/2007 | Joy et al. | |
| 7,399,313 B2 | 7/2008 | Brown et al. | |

(Continued)

*Primary Examiner* — Francis C Gray

(57) ABSTRACT

A sensor includes two coaxial RF shielding members arranged to create a coaxial RF shielding structure that is electrically open and is formed from partially enclosed cylindrical shells. The RF shielding members are spaced from one another. The sensor also includes one or multiple electrically conductive coaxial coils between the coaxial RF shielding members. This configuration creates an LC circuit without requiring a separate capacitor electrically connected to the inductor. The RF shielding structure minimizes the surrounding tissue effects (e.g., parasitic capacitance), which improves the overall accuracy of the sensor. The LC circuit also can be remotely interrogated by external reader.

48 Claims, 24 Drawing Sheets

(56) References Cited

U.S. PATENT DOCUMENTS

| | | | |
|---|---|---|---|
| 7,452,334 | B2 | 11/2008 | Gianchandani |
| 7,568,394 | B1 | 8/2009 | Keilman et al. |
| 7,647,831 | B2 | 1/2010 | Cardiomems |
| 7,677,107 | B2 | 3/2010 | Nunez et al. |
| 7,955,268 | B2 | 6/2011 | Huelskamp |
| 8,072,310 | B1 | 12/2011 | Everhart |
| 8,187,317 | B2 | 5/2012 | Leprince et al. |
| 8,372,139 | B2 | 2/2013 | Bailey et al. |
| 8,432,265 | B2 | 4/2013 | Rowland et al. |
| 8,493,187 | B2 | 7/2013 | Rowland et al. |
| 2004/0082867 | A1 | 4/2004 | Esch et al. |
| 2005/0175665 | A1* | 8/2005 | Hunter ............... A61K 45/06 424/423 |
| 2008/0033527 | A1 | 2/2008 | Nunez et al. |
| 2008/0077016 | A1* | 3/2008 | Sparks ............... A61B 5/0031 600/459 |
| 2009/0030291 | A1 | 1/2009 | O'Brien et al. |
| 2009/0105557 | A1* | 4/2009 | Najafi ............... A61B 5/0031 600/301 |
| 2010/0058583 | A1 | 3/2010 | Cros et al. |
| 2011/0257491 | A1* | 10/2011 | Robertson ........... A61B 5/0031 600/302 |
| 2013/0165801 | A1 | 6/2013 | Min |
| 2013/0197336 | A1 | 8/2013 | Flo et al. |
| 2014/0128687 | A1 | 5/2014 | White et al. |
| 2014/0273824 | A1 | 9/2014 | Fenner et al. |
| 2014/0296687 | A1 | 10/2014 | Irazoqui et al. |
| 2014/0306807 | A1 | 10/2014 | Rowland et al. |
| 2014/0350348 | A1 | 11/2014 | Tee |
| 2014/0364714 | A1* | 12/2014 | Ameri ............... A61N 1/37229 600/373 |
| 2015/0196225 | A1 | 7/2015 | Rusu |
| 2016/0029956 | A1 | 2/2016 | Rowland |

* cited by examiner

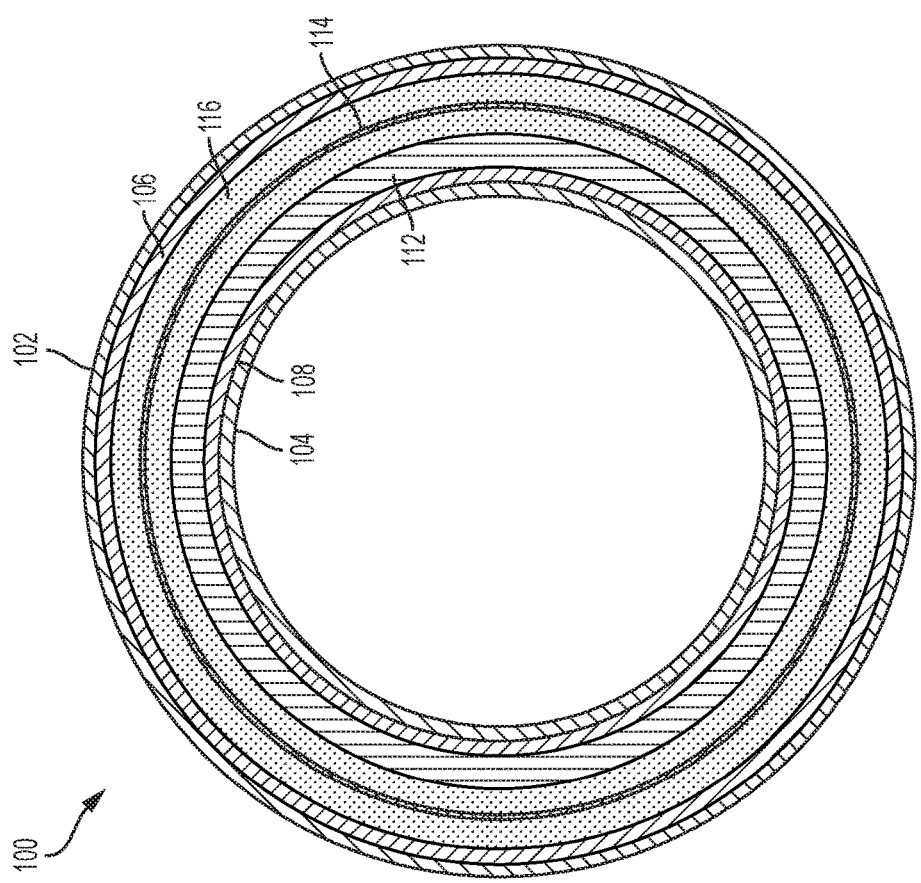

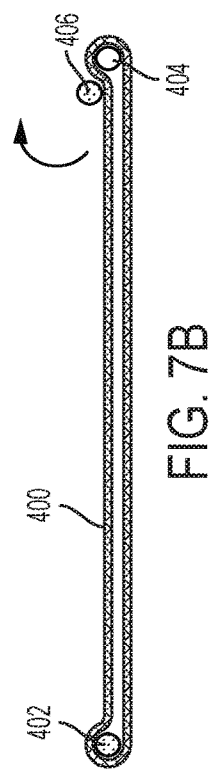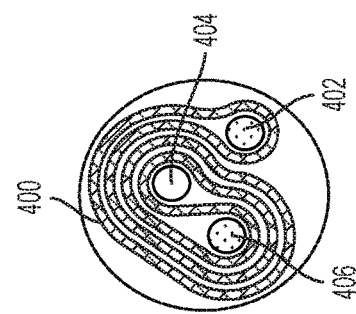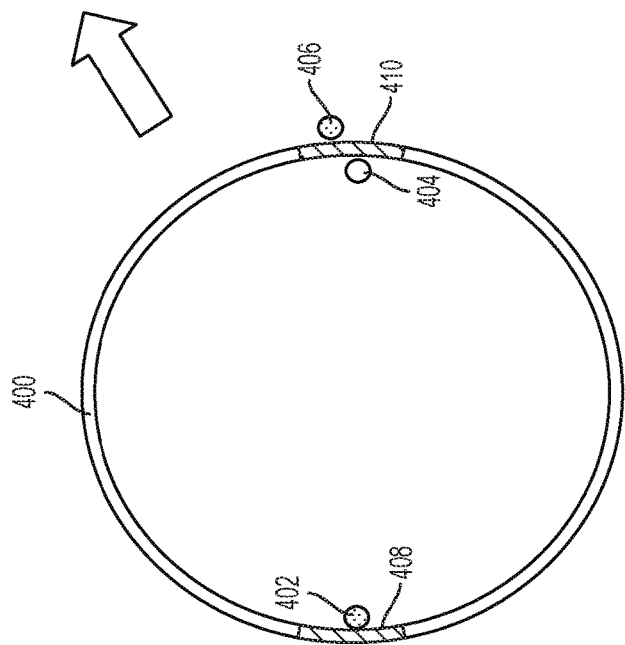

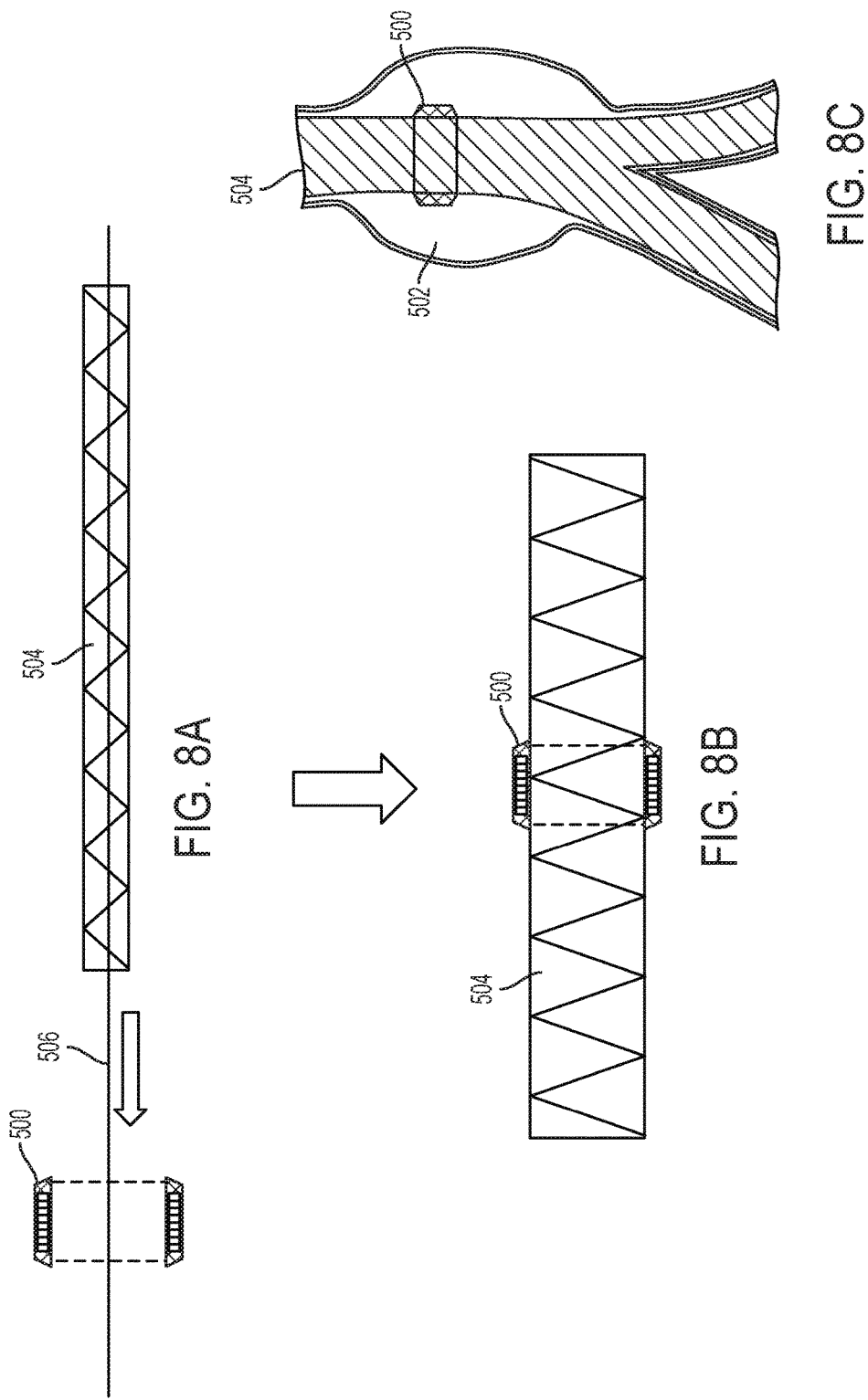

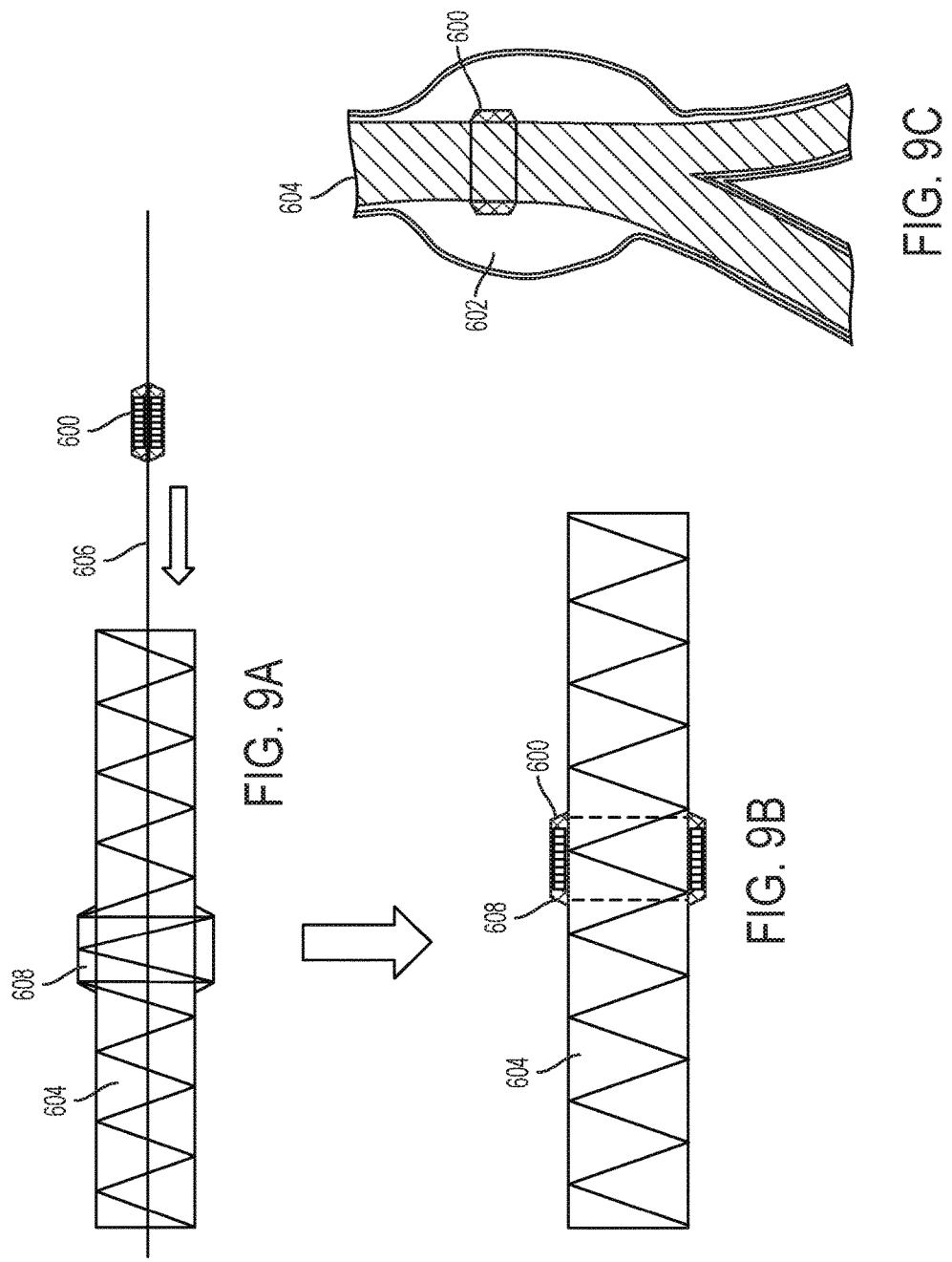

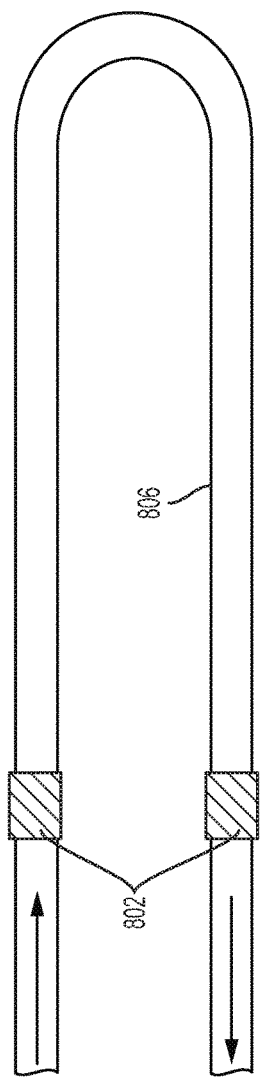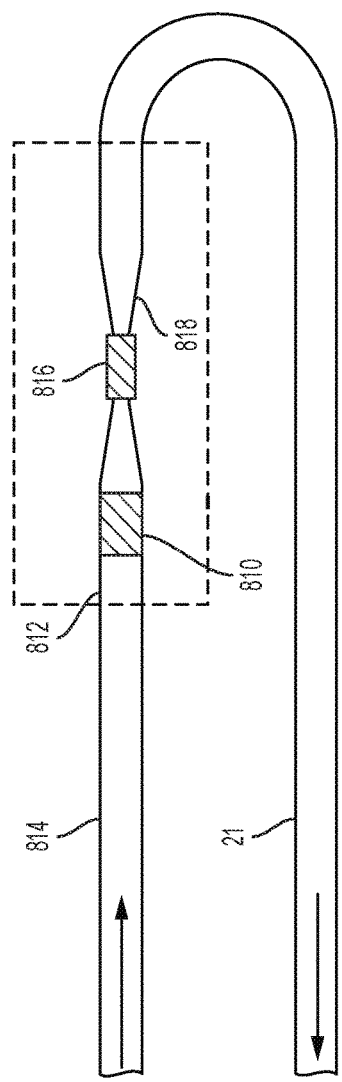

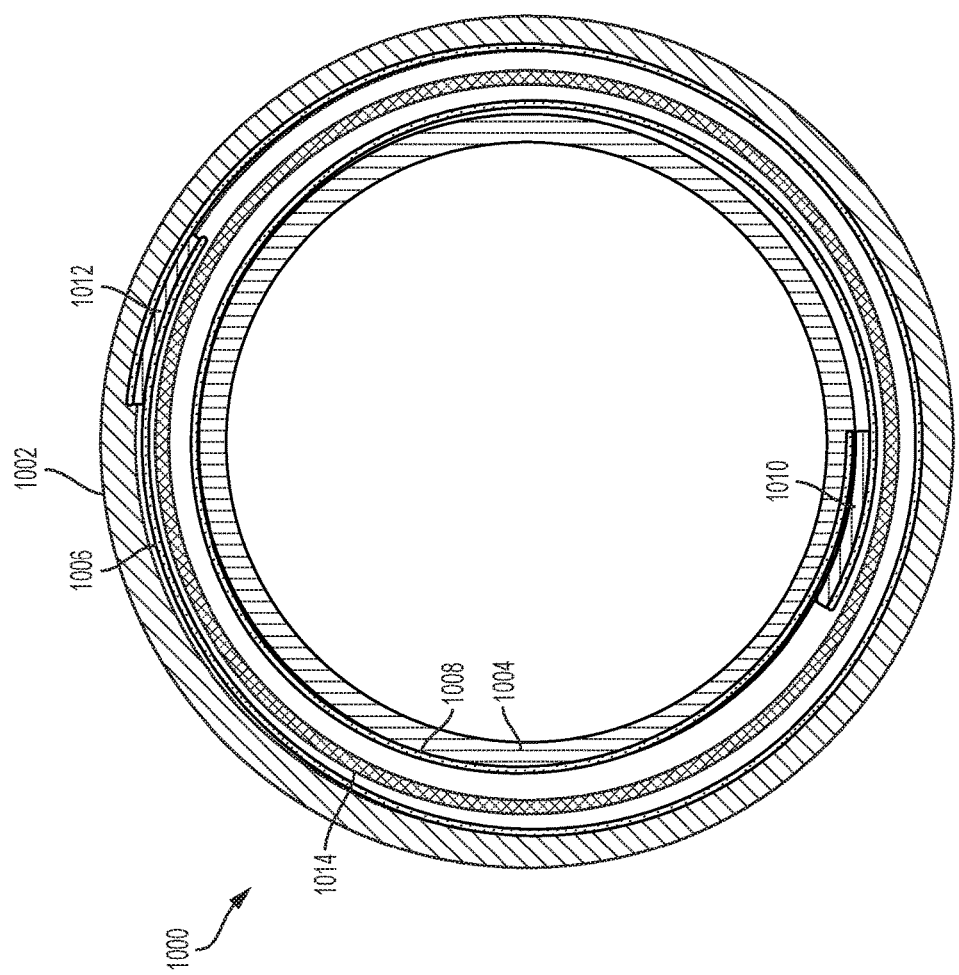

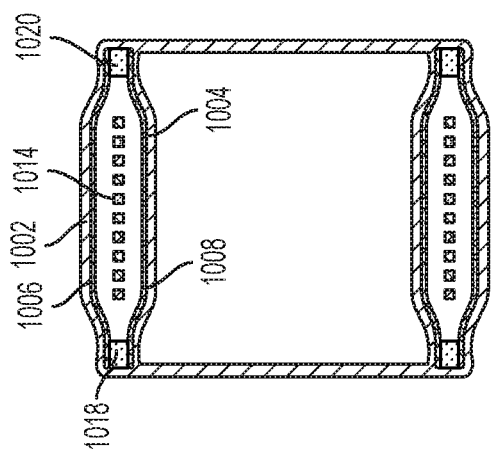
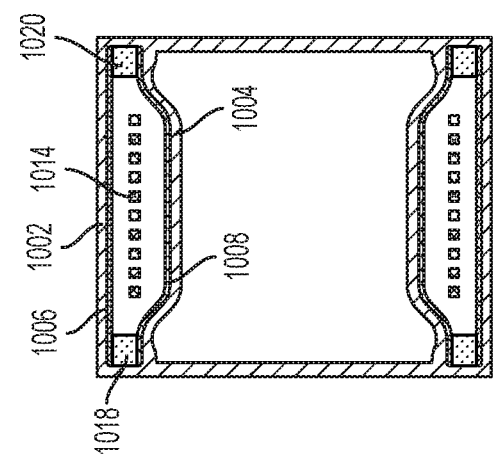
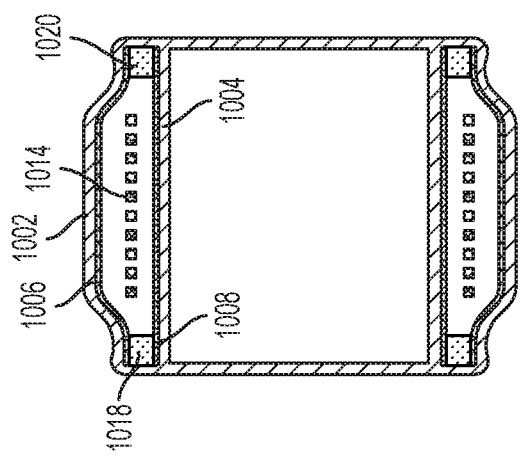

WIRELESS CYLINDRICAL SHELL PASSIVE LC SENSOR

RELATED APPLICATIONS

This application claims priority to U.S. Provisional Application No. 62/380,206, titled WIRELESS CYLINDRICAL SHELL PASSIVE LC SENSOR and filed on Aug. 26, 2016. The contents of that application (including the Appendix) are incorporated herein by reference for all purposes.

FIELD

Embodiments of the present disclosure generally relate to improved passive LC sensors for medical devices. More specifically, embodiments of the present disclosure relate to improved pressure sensors for monitoring pressure and other metrics within a blood vessel.

BACKGROUND

Measuring blood pressure is an important diagnostic tool in many medical treatments, especially when treating vascular maladies. For example, aneurysms are often treated by implanting a stent-graft within the aneurysm pocket. Measuring the blood pressure at the stent-graft can be important in tracking patient health and treatment effectiveness. Various pressure sensors have been used for measuring blood pressure within a vessel, including capacitive pressure sensors.

Some of these sensors are passive inductive-capacitive (LC) sensors. A typical LC sensor connects an inductor (L) and a capacitor (C) to form an LC resonant circuit. The capacitor may be configured to vary its capacitance in response to external pressure changes, with the LC circuit's resonant frequency changing accordingly, such that the external pressure can be determined by measuring the LC sensor's resonant frequency. One advantage of a passive LC sensor is that no embedded battery is needed, since an external radio frequency (RF) energy field may be applied to the LC circuit for wirelessly sensing, where the inductive coil serves as an RF energy receiving/transmission antenna. The wireless sensing operates through magnetic induction between the sensor antenna and the external reader antenna. This magnetic induction or coupling effect increases with increasing sensor antenna size. Therefore, in general, the bigger the sensor antenna is, the deeper the sensor can operate, despite tissue absorption of RF energy.

Several significant issues rise if these LC circuits are placed within harsh environments, such as the blood stream, without sufficient protections. One issue is that water may slowly penetrate into the sensor and change the sensor's dielectric properties, which not only drifts the resonant frequency of the sensor over time, but also decreases the signal strength due to increased RF absorption loss, eventually destroying the circuit of the sensor. Another issue is that the high dielectric property of the surrounding tissue medium induces a significant parasitic capacitance to the sensor's antenna coil, and as a result, the sensor's resonant frequency may significantly shift.

To prevent the problems discussed above, a thick, water-tight electrical insulation layer could be used to encapsulate the sensor. However, using such a layer renders the sensor bulky and impedes attachment to a stent or graft. A rigid housing could also be used to encapsulate the sensor. However, a rigid housing limits the sensor's ability to flex, creating additional difficulties when inserting the sensor and/or attaching the sensor to a stent or graft. As discussed above, a wireless passive LC sensor with a large antenna exhibits increased sensing depth in the human body. However, a large rigid antenna in the sensor impedes inserting the sensor and/or attaching the sensor to a stent or graft.

While many pressure sensors incorporate an LC circuit, they rely on electrical connections between the inductor and the capacitor. However, building the LC circuit on a flex substrate, forced-folding of the sensor for interventional delivery, and/or movement of the sensor (for example due to pressure waves caused by heartbeats), places stress on those electrical connections, causing them to fail.

Thus, several needs exist in this art for a passive LC sensor that is: thin and flexible; ready to couple to a stent or graft, particularly for the placement in a vessel without blocking the blood flow; features a large effective antenna for increased sensing distance; stable when implanted in the human body; without significant signal drift over time and without significant environmental effect on sensor performance; and biocompatible and safe in the human body.

SUMMARY

Various embodiments of the present disclosure address some or all of these issues as well as other improvements in passive LC sensors. According to one example, an LC passive sensor includes a first coaxial RF shielding element and a second coaxial RF shielding element arranged to form a coaxial RF shielding structure. The RF shielding elements are partially enclosed shells with only two opposite opens. The RF shielding elements are electrically open for wireless sensing capability and are spaced from one another, with the second RF shielding element inside the first RF shielding element. The LC passive pressure sensor also includes one or more electrically conductive coaxial coil(s) located between the first RF shielding element and the second RF shielding element. The sensor may be contained within a water barrier. This apparatus provides the functionality of a passive LC sensor with wireless sensing capability and several improvements, such as increased flexibility, improved lifetime, increased shielding, increased effective antenna size without blocking flow in a vessel, and increased sensing distance, among other advantages.

According to a first example, an apparatus comprises a first coaxial RF shielding member and a second coaxial RF shielding member arranged to form a coaxial RF shielding structure, wherein said coaxial RF shielding members are partially enclosed shells with only two opposite opens, said coaxial RF shielding members are electrically open, and said coaxial RF shielding members are spaced from one another by at least one distance and arranged such that said second coaxial RF shielding member is at least partially inside said first coaxial RF shielding member; and one or more electrically conductive coaxial coils provided between said first coaxial RF shielding member and said second coaxial RF shielding member.

In one variant, said RF shielding structure and said coil are designed to form an inductive-capacitive (LC) resonator.

In one variant, said LC resonator is adapted to have a resonant frequency within a range from 1 MHz to 50 MHz.

In one variant, said partially enclosed shells are right or oblique cylindrical shells.

In one variant, said partially enclosed shells are right or oblique cuboid shells.

In one variant, said first coaxial RF shielding member is a continuous hollow roll of conductive film.

In one variant, said conductive film is covered with electrical insulation material.

In one variant, said electrical insulation material has low water permeability.

In one variant, the ends of said roll are not electrically connected.

In one variant, said first coaxial RF shielding member is an overlapping of multiple short hollow rolls of conductive films.

In one variant, said conductive films are covered with electrical insulation material.

In one variant, said electrical insulation material has low water permeability.

In one variant, the ends of each of said rolls are not electrically connected.

In one variant, said one or more electrically conductive coaxial coils is a single layer helix coil.

In one variant, said one or more electrically conductive coaxial coils is a double-layer helix coil.

In one variant, said one or more electrically conductive coaxial coils is a multiple-layer helix coil.

In one variant, said one or more electrically conductive coaxial coils is covered with electrical insulation.

In one variant, said electrical insulation is expanded polytetrafluoroethylene (ePTFE).

In one variant, the apparatus comprises a water-barrier protection cover around said RF shielding structure.

In one variant, the apparatus comprises a sensing element between said first RF shielding member and said second RF shielding member, such that said sensing element, said shielding structure, and said coil form a wireless LC sensor.

In one variant, said sensing element is an elastomeric dielectric structure, such that said LC sensor is an LC pressure sensor.

In one variant, said LC sensor is configured and arranged to exhibit a resonant frequency that is based upon a status of said elastomeric dielectric structure.

In one variant, said dielectric structure is configured and arranged to exhibit a changed dielectric characteristic of said dielectric structure in response to applied pressure.

In one variant, said LC sensor is configured and arranged with a resonant frequency that varies in response to changes in the dielectric due to the applied pressure.

In one variant, said dielectric structure is a compressible dielectric.

In one variant, said dielectric structure is a cavity in a hermetic seal.

In one variant, said dielectric structure is porous in a hermetic seal.

In one variant, said dielectric structure is a distribution of elastic solids.

In one variant, said elastic solids are selected from the group consisting of balls, rods, pyramids, and trapezoid-prisms.

In one variant, said sensing element is a temperature-sensitive dielectric such that said LC sensor is an LC temperature sensor.

In one variant, said LC sensor is configured and arranged to exhibit a resonant frequency that is based upon a status of said temperature-sensitive dielectric.

In one variant, said dielectric is configured and arranged to exhibit a changed dielectric characteristic in response to the environmental temperature change.

In one variant, said LC sensor is configured and arranged with a resonant frequency that varies in response to changes in the dielectric due to the environmental temperature change.

In one variant, said LC sensor further comprising a crushable and expandable frame to form a crushable LC sensor.

In one variant, said crushable LC sensor has a thickness from about 0.1 mm to 1 mm.

In one variant, said frame is configured and arranged so that said LC sensor can be folded up into a compact form and then expanded post-delivery.

In one variant, said LC sensor is configured to engage a rolling supporter as it folds up.

In one variant, said rolling supporter is selected from a group consisting essentially of expanded polytetrafluoroethylene (ePTFE) rod or film.

In one variant, the apparatus comprises a flexible but non-compressible dielectric between said first RF shielding member and said second RF shielding member such that said shielding structure and said coil form a wireless LC sensor for sensing diameter or size.

In one variant, said LC sensor is configured and arranged to exhibit a resonant frequency that is based upon a diameter or size of said sensor.

In one variant, said LC sensor is configured and arranged with a resonant frequency that varies in response to the change of said LC sensor diameter or size.

In one variant, the apparatus comprises a MEMS sensor with an ASIC between said first RF shielding member and said second RF shielding member such that said coil is configured and arranged as the transceiver antenna of said MEMS sensor.

In one variant, said coil receives externally delivered RF energy and supplies that energy to said MEMS sensor.

In one variant, said coil is transmitting an RF signal from said MEMS sensor.

In one variant, the apparatus comprises a water-barrier cover.

According to a second example, a method of measuring flow in a graft comprises: imbedding a first passive LC pressure sensor in a middle portion of a narrowed section within said graft, wherein said first LC sensor is configured to produce a first signal that is a function of liquid pressure within said graft; imbedding a second passive LC pressure sensor at an end of said narrowed section, wherein said second LC sensor is configured to produce a second signal that is a function of liquid pressure within said graft; and collecting and analyzing said first signal and said second signal to determine the flow through said graft.

According to a third example, a method of introducing a passive LC sensor lying on the outer surface of a treatment stent-graft into a vascular lumen, comprises the steps of: introducing a self-expanding passive LC sensor in a folded configuration to a selected site in a vascular lumen; releasing the self-expanding passive LC sensor to allow the self-expanding passive LC sensor to expand from the folded configuration at the selected site in said vascular lumen; passing a self-expanding treatment stent-graft in a folded configuration through a lumen of said expanded LC sensor to the selected site in said vascular lumen; adjusting a location of said LC sensor relative to said stent-graft; and releasing the self-expanding treatment stent-graft to allow the self-expanding treatment stent-graft to expand from its folded configuration at the selected site in said vascular lumen with the LC sensor laying on the outer surface of said stent-graft.

According to a fourth example, a method of introducing a passive LC sensor lying against an inner surface of a treatment stent-graft into a lumen, comprises the steps of: providing a folded self-expanding treatment stent-graft;

introducing said folded self-expanding stent-graft to a selected site in a vascular lumen; expanding the self-expanding stent-graft at the selected site in said vascular lumen; providing a folded self-expanding passive LC sensor; introducing said folded self-expanding passive LC sensor through the lumen of said expanded stent-graft at the selected site in the vascular lumen; and expanding the self-expanding LC sensor so that it lays against the inner surface of said stent-graft.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 illustrates a cut away view from an axial perspective of the exemplary pressure sensor of FIG. 3.

FIGS. 7a-7c illustrate an exemplary pressure sensor as it is crunched or folded into its delivery profile, according to embodiments of the present disclosure.

FIGS. 8a-8c illustrate an exemplary pressure sensor as it is coupled to the exterior of a stent-graft and placed within a vessel, according to embodiments of the present disclosure.

FIGS. 9a-9c illustrate an exemplary pressure sensor as it is coupled to the interior of a stent-graft and placed within a vessel, according to embodiments of the present disclosure.

FIGS. 11a-11b illustrate two exemplary pressure sensors to measure differential flow, according to embodiments of the present disclosure.

FIG. 13 illustrates a cut away view from an axial perspective of an exemplary pressure sensor, according to embodiments of the present disclosure.

FIGS. 14a-14c illustrate cut away views from a longitudinal perspective of the exemplary pressure sensor of FIG. 13.

DETAILED DESCRIPTION

Figure 1:
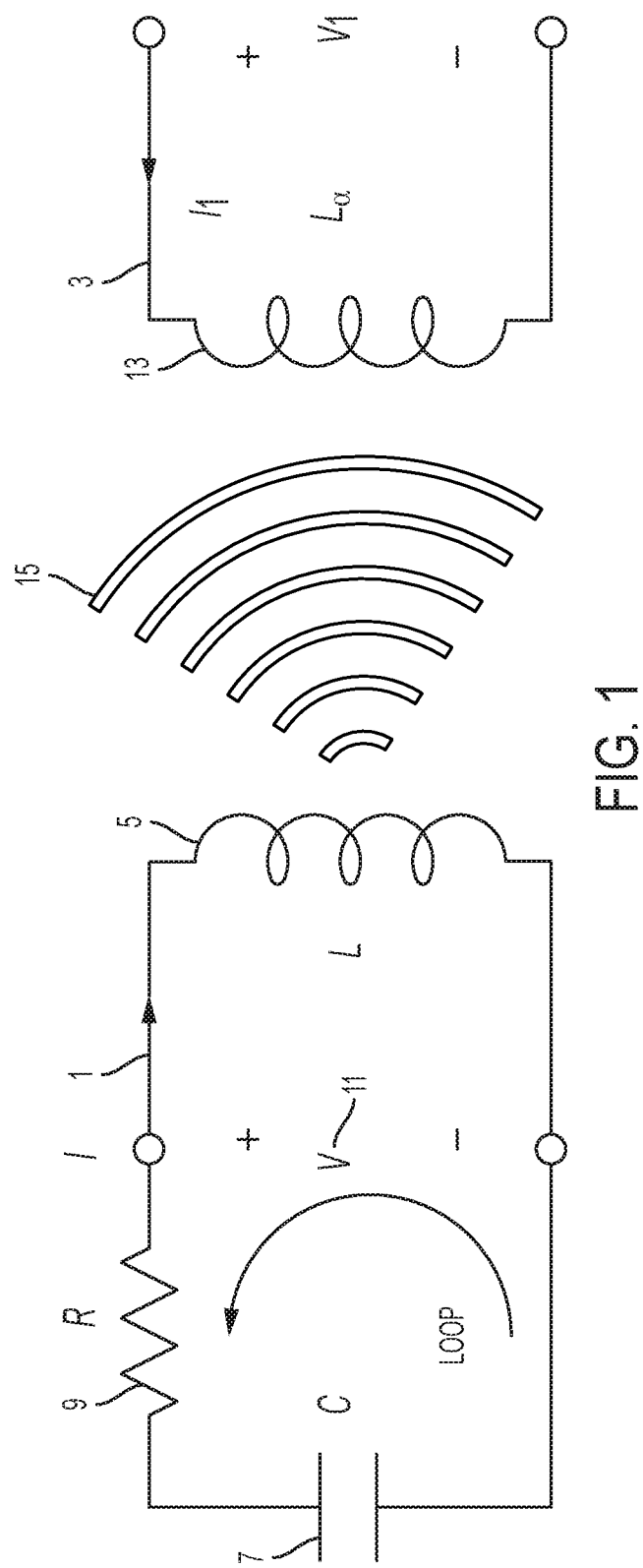
FIG. 1 illustrates a diagram of an exemplary LC tank circuit and a portion of an exemplary circuit for a reader, according to embodiments of the present disclosure.

According to some embodiments, FIG. 1 shows an electrical equivalent resonant circuit 1 of a passive LC sensor with an equivalent capacitor C (reference number 7) and inductor L (reference number 5), and an equivalent electrical circuit 3 of a sensor reader, where the reader antenna 13 wirelessly measures the resonant frequency of circuit 1 by magnetic induction between the sensor antenna (e.g., the inductor 5) and reader antenna 13. The electrical equivalent resonant circuit 1 can also be referred to as an LC circuit, LC tank or LC tank circuit, because of the voltage 11 that it can store. The LC tank 1 has a resonant frequency that depends on the inductance and capacitance provided by the inductor 5 and capacitor 7, respectively. If the capacitor 7 is configured to vary its capacitance in response to changes in pressure or other parameters within a vessel (such as temperature), the LC circuit 1 can serve as a pressure sensor or a temperature sensor accordingly.

As one of skill in the art will readily appreciate, there are a wide variety of electrical components that exhibit capacitive and inductive characteristics and that can be used in various embodiments discussed herein. As also shown in FIG. 1, the LC circuit 1 also includes an equivalent resistor 9 that represents energy loss due to, e.g., RF absorption. In general, a smaller resistance is required to provide a higher quality factor (Q, e.g., greater than 35) so that the resonance ring-down signal 15 from the sensor can last long enough for the reader to pick up the resonance signal.

One of the benefits of an LC tank (e.g., LC tank 1 in FIG. 1) is that characteristics of that circuit (e.g., resonant frequency) can be determined without needing to include a power source, such as a battery, as part of the sensor circuit. Instead, an external reader or monitoring tool (e.g., equivalent electrical circuit 3 in FIG. 1) can interact wirelessly with that circuit to detect those characteristics of the LC tank 1. These advantages render the LC tank 1 as a suitable candidate for a pressure sensor for wirelessly monitoring blood pressure within a vessel.

For example, if a dielectric material that reacts to external pressure is placed within the capacitor (e.g., capacitor 7 in FIG. 1), a change in blood pressure will cause a change in capacitance in the LC tank 1, which results in a change in its resonant frequency.

For another example, the LC tank 1 may be set up so that the plates of the capacitor move in response to external pressures, which will affect the capacitance and the resonant frequency of the LC tank 1. Under either approach, if the other characteristics of the LC tank 1 (e.g., inductance) remain relatively constant, the change in the resonant frequency can be used to determine the change in capacitance, which can then be used to determine a measurement of the blood pressure within the vessel.

Figure 2:
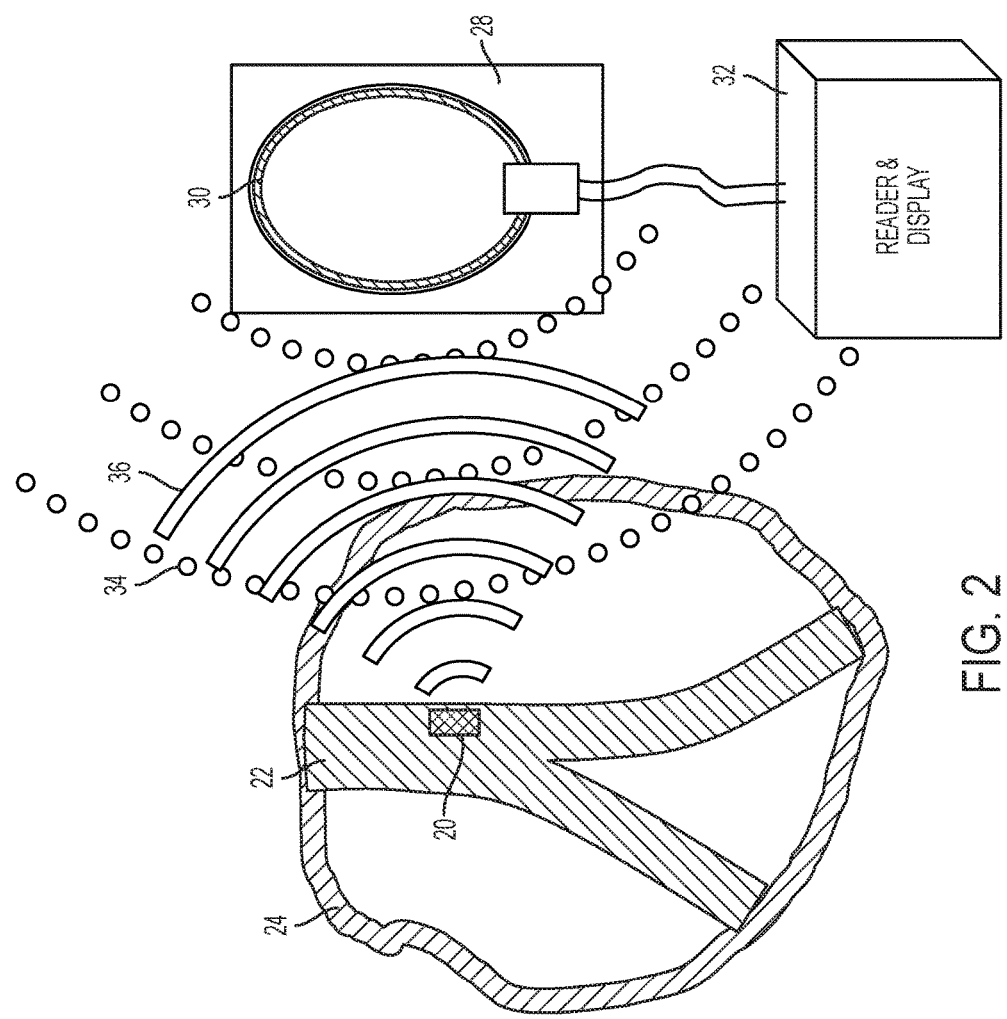
FIG. 2 illustrates an exemplary pressure sensor coupled to a stent-graft as well as an exemplary measuring tool, according to embodiments of the present disclosure.

These approaches can be seen in FIG. 2, in which a pressure sensor 20 uses an LC circuit to monitor blood pressure at a stent-graft 22 placed to treat an aneurism in the body 24. In various embodiments, the pressure sensor may be placed on an outer surface of the stent-graft, an inner surface of the stent-graft, or may be integrated within the stent-graft. Thus, measuring blood pressure at the stent-graft includes measuring blood pressure outside of the stent-graft and/or within the stent-graft. The measuring device 28 includes an antenna 30 and a reader/display 32. The reader/display 32 can include a processor, memory, and other hardware and/or software needed to measure signals from the antenna 30 and process those signals to determine (and perhaps display) the blood pressure measurements. The measuring device 28 emits a pulse 34, which causes the pressure sensor to emit a ring-down signal 36. The measuring device 28 analyzes the ring-down signal 36 to identify pressure within the stent-graft 22.

Figure 3:
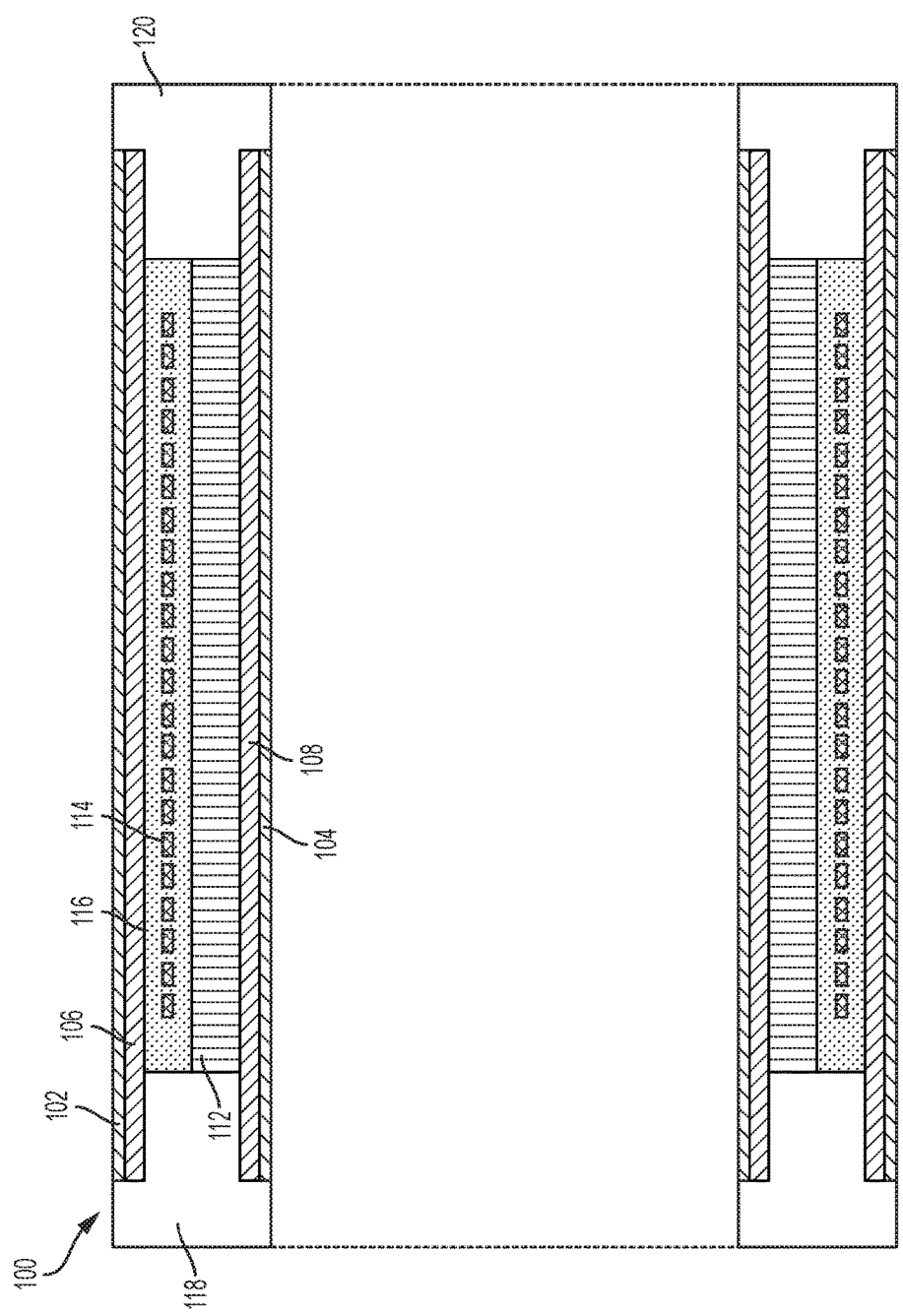
FIG. 3 illustrates a cut-away view from a lateral perspective of an exemplary pressure sensor, according to embodiments of the present disclosure.

Referring now to FIGS. 3 and 4, a sensor 100 is a partially RF-shielded, water barrier protected, double-shell LC resonator, which provides increased flexibility and longevity. The drawings are for illustration only and are not in proportion. The sensor 100 in these figures includes an outer water barrier cover 102 and an inner water barrier cover 104. These covers 102, 104 may be non-conductive, thin, dense PTFE films with a thin silicone or hydrophobic coating. Between those water barrier covers 102, 104 are RF shielding layers 106, 108. The RF shielding layers 106, 108 (also referred to as RF shielding members) can be formed from a metalized film and create a cylindrical shell to protect the other components of the sensor 100. In some embodiments, one or more RF shielding layers form right or oblique cylindrical shells. In some embodiments, one or more RF shielding layers form right or oblique cuboid shells.

In some embodiments, an RF shielding layer may be a continuous hollow roll of conductive film (e.g., a continuous hollow roll of an electrically-insulated metalized film) or an overlapping of multiple short or partial hollow rolls of conductive film, such that each RF shielding layer is electrically open (as discussed below in more detail). Alternative shielding materials may include thin conductive sheets, woven fine-wire fabrics, or other flexible and conductive materials. The RF shielding layer may also be covered with an electrical insulation material that has low water permeability, such as ePTFE.

In some embodiments, the two RF shielding members 106, 108 are coaxial RF shielding members. The coaxial RF shielding members are not electrically connected, which makes it possible to apply external RF energy to excite the resonant circuit of the sensor and then detect resonant signals from the sensor with an external antenna. In other words, in these embodiments, the cylindrical shell structure of the RF shielding layers allows the sensor to have RF shielding on its cylindrical surfaces without the loss of magnetic induction for wireless energy delivery and signal transmission. In some embodiments, the two RF shielding layers 106, 108 are separated by a constant distance (e.g., a radial distance) while in other embodiments, the distance between the two RF shielding layers 106, 108 varies. For example, this gap distance can be from about 50 to 100 micrometers for flexibility, or up to about 1 mm if crush-loading is not required.

The sensor 100 also includes a sensing structure or sensing element 112 located between the RF shielding layers 106, 108. As shown in FIGS. 3 and 4, the sensing element 112 contacts the inner surface of the RF shielding layer 108. In some embodiments, sensing element 112 can be an elastomeric dielectric layer or a hermetic-sealed cavity for sensing pressure (discussed below), or a temperature-sensitive dielectric layer for sensing environmental temperature. In some embodiments, an elastic dielectric layer or cavity for sensing pressure, or a temperature-sensitive dielectric layer for sensing temperature, may be located between two coil layers of a double-layered coil (e.g., of coil 114 discussed below), between an outer coil layer (e.g., of coil 114 discussed below) and the RF shielding layer 106, or between the inner coil layer (e.g., of coil 114 discussed below) and the RF shielding layer 108. The dielectric material may be elastomeric, compressible, or otherwise formed from a material that exhibits changed dielectric properties in response to changed pressures. As a result, the dielectric structure may be an elastomeric dielectric structure, a compressible dielectric structure, or the like. In some embodiments, the dielectric material is a distribution of elastic solids taking the shapes of balls, rods, pyramids, and trapezoid-prisms.

Continuing inward, the sensor 100 includes a coil 114, which may be a single wire or stripe coil enveloped in an electrical insulator such as ePTFE 116. For example, the ePTFE 116 may form a thin film in which a conductor is enveloped. Exemplary techniques for constructing a thin, filled ePTFE film are discussed in U.S. Pat. No. 4,187,390 to Gore and U.S. Pat. No. 4,985,296 to Mortimer, Jr. The wire or stripe itself may be insulated by wrapping the wire or strip in a thin layer of ePTFE film.

In some embodiments, the sensor 100 includes a double-layered coaxial inductive helix coil 114 between the RF shielding layers 106, 108. The coil 114 can be formed by winding a single conductive wire or stripe from left to right for the inner coil layer and then continuously winding back from right to left for the outer coil layer, where initial and terminal ends of the coil 114 are not connected. This coil 114 is electrically isolated, meaning that it does not contact or form a direct electrical connection with any other conductive component or itself. In some embodiments, the sensor 100 includes a single layer of inductive helix coil 114. The coil 114 can be formed through winding a single conductive wire or stripe from left to right, where two ends of the coil 114 are not connected. As discussed in more detail below, the inductance L of the coil 114 and the capacitance C between the coil 114 and RF shielding layers 106, 108 form an electrically resonant LC circuit. In some embodiments, the LC circuit has a resonant frequency within a range of about 1 MHz to 50 MHz. Thus, in some embodiments, one or more electrically conductive coaxial coils (e.g., coil 114) along with RF shielding layers (e.g., RF shielding layer 106, 108) form an inductive-capacitive (LC) resonator.

In some embodiments, donut-shaped caps may be placed on the ends 118, 120 to prevent liquids from contacting components 106-114 between the water barrier covers 102, 104. The caps and the water barrier covers 102, 104 form a water-tight seal. In some embodiments, each of the elements 104, 106, 118 and 120 may be formed of, or covered by, the same water barrier materials, such as dense PTFE films (for example, with a thickness of 10-30 micrometers), in which case FEP adhesives may be used to bond them together. In some embodiments, an extra silicone or hydrophobic coating may be added on the outer surfaces of elements 104, 106, 118 and 120. In some embodiments, the outer water barrier cover 102 and the inner water barrier cover 104 are omitted, and the RF shielding layers (along with the caps) provide a water-tight enclosure for the components between the RF shielding layers 106, 108.

To maintain flexibility, in some embodiments, the diameter of the coil wire with insulation can be from about 25 to 100 micrometers, and the thickness of RF shielding layers 106, 108 can be about 25 micrometers or less. In some embodiments, the thickness of sensing element 112 can be from about 25 to 100 micrometers, and the overall thickness of the sensor 100 can be as small as about 100 to 200 micrometers or from about 0.1 mm to 1 mm.

Figure 5C:
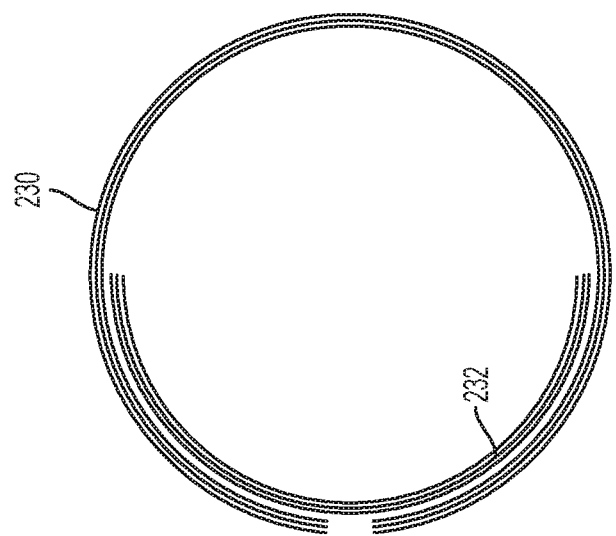
FIGS. 5a-5c illustrate aspects of an exemplary RF shielding element, according to embodiments of the present disclosure.
Figure 5B:
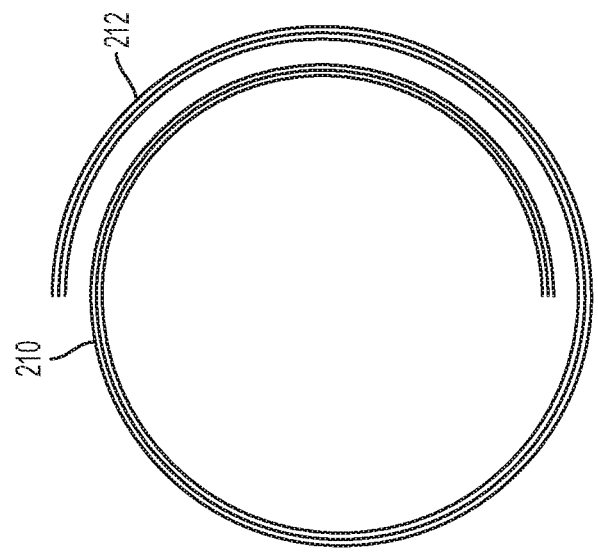
Figure 5A:
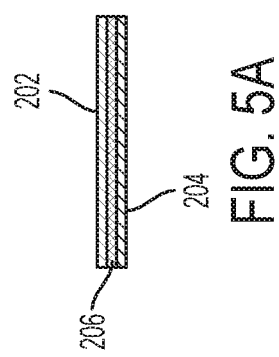

Additional details about the RF shielding layers are shown in FIGS. 5a-5c. As shown in the abbreviated cross section of FIG. 5a, to make an RF shielding layer, a conductive sheet 206 is first bonded with electrical insulation layers (such as ePTFE) 202 and 204 by adhesives (such as FEB). Then, wrapping or rolling the sheet forms a cylindrical shielding layer as shown in FIGS. 5b & 5c. FIG. 5b shows an RF shielding layer 210 in isolation and rotated to see its side profile. The RF shielding layer 210 is a single, unitary layer with a cylindrical profile. However, this layer 210 is electrically isolated (the gap is filled with electrical insulation as shown in FIG. 5a, but not shown in FIG. 5b) and is not in electrical contact with either itself (i.e., it does not form a closed loop) or with other electrical components (such as the coil 114). A portion 212 of the layer 210 overlaps itself, though this portion 212 is still spaced apart from the rest of the layer 210 to prevent a closed circuit. FIG. 5c shows a similar setup in which two shielding layer portions 230, 232 are placed in a coaxial relationship. As can be seen in FIG. 5c, neither portion contacts the other (i.e., they are maintained a distance apart, and the gap between them is filled with electrical insulation as shown in FIG. 5a, but not shown in FIG. 5c) or forms a closed loop.

This configuration provides a number of advantages. First, the RF shielding and the coil interact, not through direct electrical connections but instead through distributive capacitance coupling. Thus, the coil (e.g., coil 114 in FIG. 3) provides the inductance (L) for the sensor while the distributed capacitance provides the capacitance (C) for the sensor. As a result, the sensor includes an LC circuit without requiring a separate capacitor electrically connected to the inductor. In some embodiments, the inductance L of the coil 114 and the capacitance C between the coil layers and/or RF shielding layers 106, 108 form an electrically resonant LC circuit. By eliminating electrical connections between an inductor and a capacitor, which are vulnerable to breaking, the sensor 100 creates a more reliable mechanical and electrical structure that increases its lifespan. Furthermore, for such a unique LC configuration, the electrical parameters (including resonant frequency, quality factor, and power level, among others) can be manipulated, by (1) putting one or multiple isolated coils between the RF shielding layers, (2) changing the number of coil turns, and (3) using different layouts of multiple coils, such as in parallel, in series, interleaved, or overlaid.

In addition, the RF shielding reduces the surrounding tissue effects (e.g., parasitic capacitance), which improves the overall accuracy of the sensor 100. At the same time, the RF shielding still permits remote devices to interrogate the sensor 100. The water barrier cover, as well as the metal shielding layer, helps to minimize or prevent liquid penetration into the circuit, which prevents signal drift over time and increases long term survival in the human body.

Furthermore, this design enables a thin, flexible, and foldable pressure sensor. In some embodiments, the thickness of the sensor 100 is between 0.1 mm and 1.0 mm. For example, a sensor with a thickness of 0.2 mm can be put into a peripheral small vessel with a diameter of 5 mm, in which the sensor occupies about 16% of the lumen cross-section area, and only along the lumen wall, such that it doesn't block the major flow at the lumen center. Such a sensor can be folded down to 6 Fr or less for interventional delivery. For another example, a sensor with a thickness of 0.3 mm can be put into one major trunk of pulmonary artery with a diameter of 25 mm, in which the sensor occupies 8% of the cross-section area of the vessel lumen, and only along the lumen wall, such that it doesn't block the major flow at the lumen center. Such a sensor can be folded down to 10 Fr or less for interventional delivery.

Figure 6A:
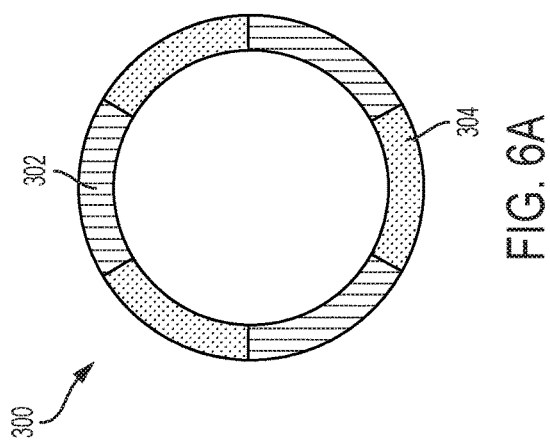
FIGS. 6a-6b illustrate exemplary sensor elements along a cut away view from an axial perspective, according to embodiments of the present disclosure.

In some embodiments, as shown in FIG. 6a, a sensing element 300 (which may be used as, for example, the sensor element 112 in FIGS. 3 and 4), may only be partially responsive to external changes. For example, some zones 304 (also referred to as elastic zones) of the sensing element 300 incorporate elastic sensing materials that respond to environmental pressure changes, while other zones 302 are formed of materials that do not respond to environmental pressure changes. Similar zones may be constructed for sensing temperature changes or other parameters.

Figure 6B:
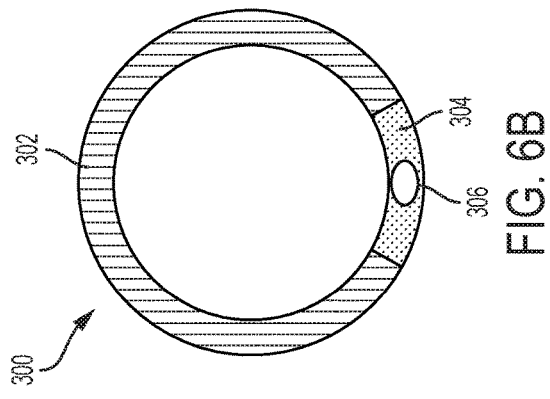
Figure 6C:
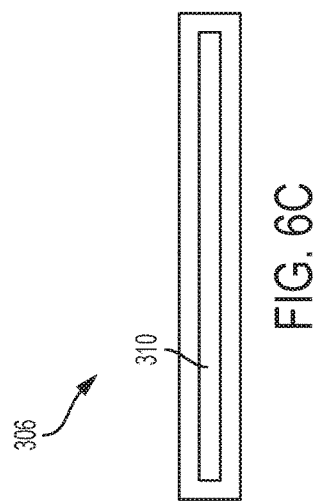
FIGS. 6c-6d illustrate cut away views from a lateral perspective of a hermetic cavity, according to embodiments of the present disclosure.
Figure 6D:
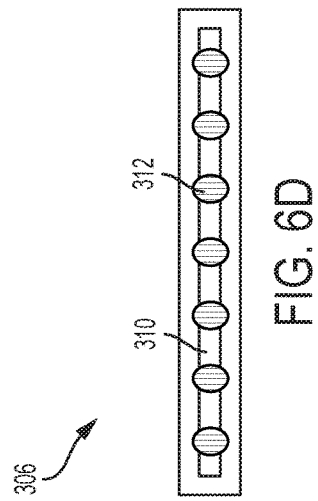

For absolute pressure sensing, a small hermetic sealed cavity 306 may be embedded into an elastic zone 304, as shown in FIG. 6b. The hermetic cavity 306 could be created by laminating three layers of low temperature, co-fired ceramics (LTCC) and cutting out a center portion of the middle layer. FIG. 6c shows a cut away view from a lateral perspective of the hermetic cavity 306 of sensor element 112, in which 310 is empty space. In some cases, elastic supporters 312 may be added into the cavity 310 as shown in FIG. 6d. When external pressure is increased, the top and bottom layer of the cavity are first pushed closer to each other, and then the RF shielding layers are pushed closer together, to cause the change of the resonant frequency of the LC circuit. In some embodiments, the dielectric structure may be a cavity in a hermetic seal or may be porous in a hermetic seal.

Overall, the sensors in these embodiments create a wireless, unpowered, passive mechanism for monitoring pressure, temperature, flow and/or stenosis of the stent or graft, as well as other physiological information within the human body. Particularly, the cylindrical nature of the shell makes it especially amenable to integration with a cylindrical stent or graft. In some cases, a sensor may be directly built into the wall of, for example, an arteriovenous (AV) graft, which may be surgically implanted into a human body. In other cases, a sensor may be folded into a compact configuration and then deployed and expanded at site through interventional delivery. The sensor can be remotely interrogated, and offers stable measurements with no significant signal drift over time. Moreover, it is biocompatible and safe, and can stay inside the body over the lifetime of the patient.

In some embodiments, the dielectric material is a flexible but non-compressible dielectric material located between the two RF shielding members. In these embodiments, the shielding structure and coil form a wireless LC sensor for sensing diameter or size, as the resonant frequency is based on the sensor diameter or size and will vary in response to changes to the sensor diameter or size.

In some embodiments, the sensor or sensor element is a MEMS sensor with an ASIC between the RF shielding members, such that the coil operates as the transceiver antenna of the MEMS sensor. In these embodiments, the coil receives externally delivered RF energy to the MEMS sensor and also transmits RF signals originating from the MEMS sensor.

In some embodiments, the sensor includes a crushable and expandable frame. The frame enables the sensor to be folded-up into a compact form and then expanded (e.g., self-expanded) after delivery.

FIGS. 7a-7c illustrate how a sensor 400 can be folded into its delivery profile around a reserved lumen 404 (for insertion of a guide wire) with the help of PTFE rolling rods or supporters 402 and 406. Those rods or supporters may be ePTFE rods or films. The sensor at contact areas 408, 410 may not have any sensing material, so that the folding stress on these areas will not damage the sensing material. The sensor may be folded up into a triple or multi-lobed configuration or other compact shapes. Thus, in some embodiments, a crushable LC sensor folds up into a compact form and then expands post-delivery.

FIGS. 8a-8c illustrate how a sensor 500 may be deployed into an aneurysm sack 502 over a stent-graft 504. As shown in FIG. 8a, the sensor 500 travels over a guidewire 506, for example, in its compressed state. As also shown in FIG. 8a, a stent-graft 504 can travel along that same guidewire 506. Upon arrival in the aneurysm sack 502, the sensor 500 expands to its expanded state and the stent-graft 504, which has also expanded into its expanded state, passes into the sensor 500 until it reaches the configuration shown in FIG. 8b. At that point, the sensor 500 is secured to the stent-graft 504, which is secured within the aneurysm sack 502, as shown in FIG. 8c. Alternatively, the stent-graft 504 may pass into the sensor 500 in its folded state and then expand. The expansion forces of the stent-graft 504 may secure (in whole or in part) the sensor 500 to the stent-graft 504.

FIGS. 9a-9c illustrate how a sensor 600 may be deployed into an aneurysm sack 602 within a stent-graft 604. As shown in FIG. 9a, the sensor 600 travels over a guidewire 606, for example, in its compressed state. As also shown in FIG. 9a, a stent-graft 604 can travel along that same guidewire 606. Upon arrival in the aneurysm sack 602, the stent-graft 604 expands to its expanded state and the sensor 600 passes through the stent-graft 604 until it reaches the configuration shown on the left side of FIG. 9a, expanding and creating a bulge 608 in the graft. At that point, the sensor 600 is secured to the stent-graft 604, which is secured within the aneurysm sack 602, as shown in FIG. 9c.

Figure 10B:
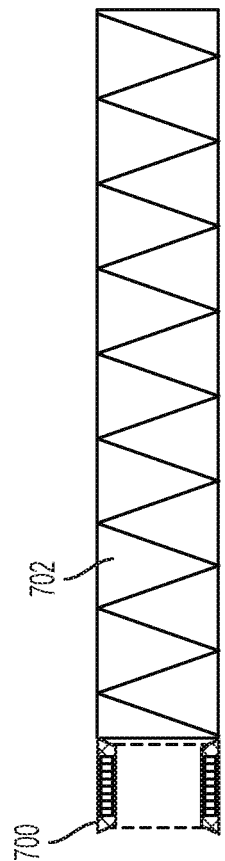
FIGS. 10a-10b illustrate an exemplary pressure sensor as it is coupled to an end of a stent-graft and placed within a vessel, according to embodiments of the present disclosure.
Figure 10A:
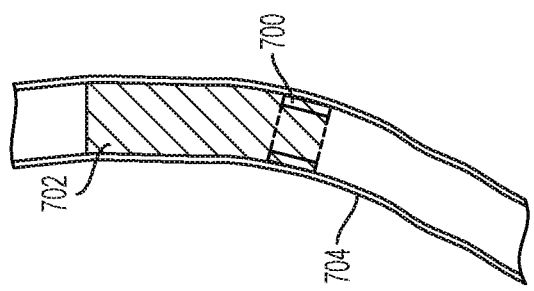

As shown in FIGS. 10a-10b, similar techniques may be used to attach a sensor 700 to an end of a stent 704, which is secured within a vessel. Thus, in some embodiments, a passive LC pressure sensor may be integrated with an expandable stent frame either at an end or in the middle of the stent, such that the sensor can be delivered in a folded-up compact shape and then expanded post-delivery along an interventional delivery catheter. In other embodiments, a passive LC pressure sensor is integrated with a vascular treatment stent, such that the sensor and treatment stent can be delivered in a folded-up compact shape and then expanded post-delivery along an interventional delivery catheter.

In some embodiments, two passive LC sensors are integrated, one near each end of a stent or graft. The two sensors may have different inductances or capacitances on the same external pressure load, such that their resonant frequencies are different, making it easy to separate the signals during measurement. In another embodiment, two passive LC pressure sensors are integrated on a graft that has a narrowed section. One sensor is in the middle of the narrowed section and the other is located nearby. Two pressure measurements from these two sensors can be used to calculate the flow through the graft using a differential pressure method.

Aspects of these embodiments can be seen in FIGS. 11a-11b. For example, in FIG. 11a, two sensors 802 are placed at two different locations on a graft 806. Pressure measurements from these two sensors can then be used to detect any occlusion that may exist between those two locations. This technique can also be useful in situations where a graft 806 has a non-uniform width. For example, and as shown in FIG. 11b, a first sensor 810 is placed over a wider section 812 of the graft 814, and a second sensor 816 is secured to a narrower section 818 of the graft 814. Pressure measurements from these two sensors can then be used to determine blood flow between those two locations. This can be particularly useful to determine a degree of occlusion within or near the graft 814 and/or the narrower section 818 of the graft 814.

Figure 12B:
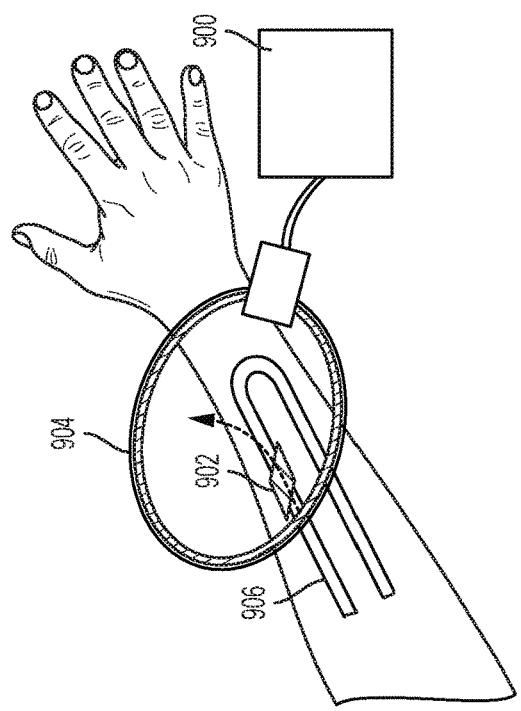
FIGS. 12a-12b illustrate an exemplary measurement technique, according to embodiments of the present disclosure.
Figure 12A:
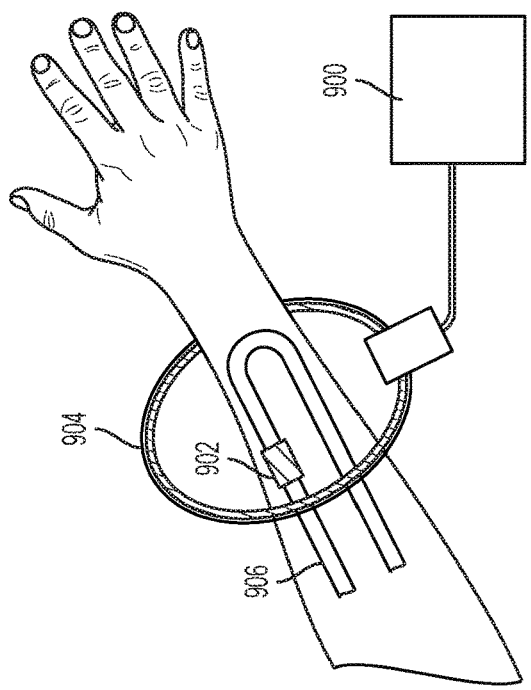

FIGS. 12a-12b illustrate how a measurement tool 900 can be used to extract a pressure measurement from a sensor 902. The antenna 904 of the measurement tool 900 passes over the sensor 902, which is secured to a graft 906 within the patient. The antenna 904 transmits energy to the sensor 902, which responds by emitting RF energy at its resonant frequency. The antenna 904 detects this energy, determines the resonant frequency, and then computes the pressure within the graft 906. Alternatively, the antenna 904 may transmit energy along a spectrum of frequencies at different times, and monitor for when the sensor 902 begins to absorb energy, which will correspond to its resonant frequency.

FIGS. 13 and 14a-14c illustrate aspects of another exemplary sensor 1000. As shown in FIG. 13, this sensor 1000 includes an outer water barrier 1002 and an inner water barrier 1004. These water barriers may also be electrically insulating. Contacting inner surfaces of the water barriers 1002, 1004, respectively, are RF shielding layers 1006, 1008. Each of these layers is secured to itself by adhesives 1010, 1012 that form water impermeable and electrical insulating connections between different portions of the RF shielding layers 1006, 1008. In this manner the RF shielding layers 1006, 1008 can be electrically isolated yet mechanically secure. In some embodiments, the RF shielding layers 1006, 1008 and the adhesives 1010, 1012 themselves form a water barrier, such that additional water barrier layers (e.g., 1002, 1004) are not required. Within the RF shielding layers 1006, 1008 is a coil 1014. While not shown in FIG. 13, a dielectric layer can also be included. FIGS. 14a-14c illustrate vertical cross sections of the sensor 1000, illustrating its flexible nature, as well as the ends 1018, 1020 of the sensor 1000. The sensor's ends near 1018 and 1020 can be thinner than the middle of the sensor, since there are no coils or sensing structures at either end. The sensor's inner surface can be flat while the outer surface is curved, as shown in FIG. 14a-. The sensor's outer surface can be flat while the inner surface is curved, as shown in FIG. 14b. Both the inner and outer surfaces can be curved, as shown in FIG. 14c.

Figure 15A:
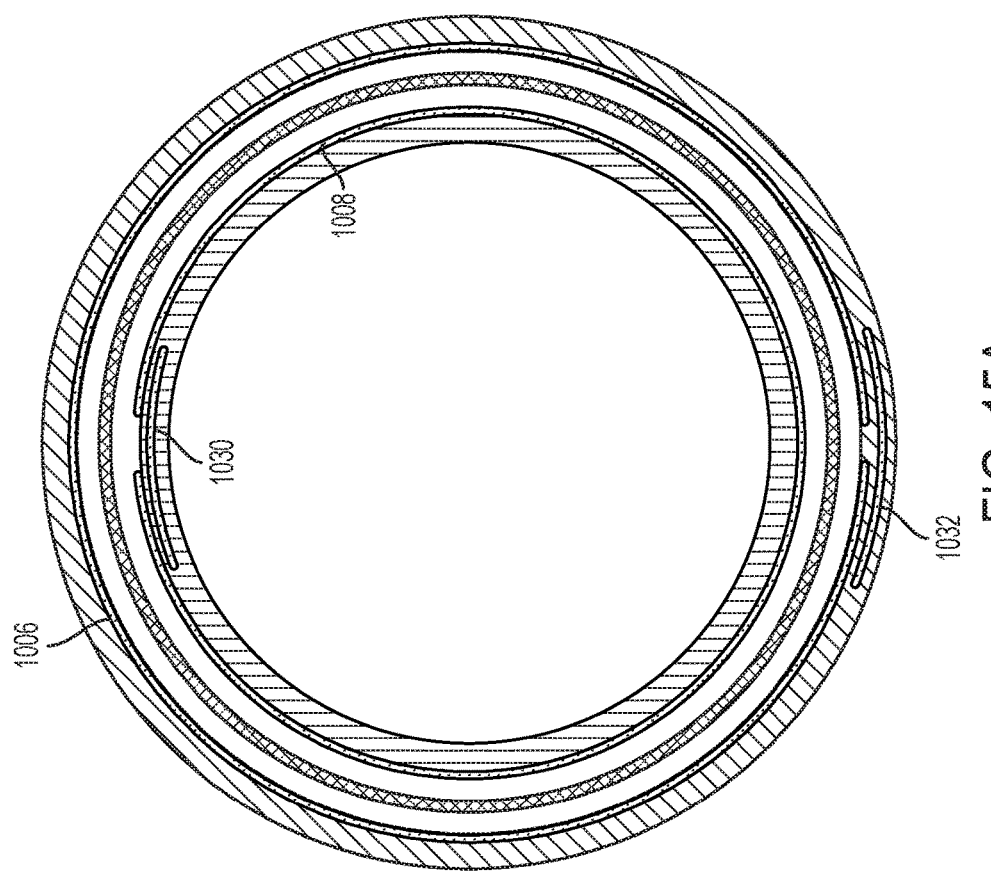
FIGS. 15a-15c illustrate a cut away view from an axial perspective of exemplary pressure sensors with different RF shielding members, according to embodiments of the present disclosure.
Figure 15B:
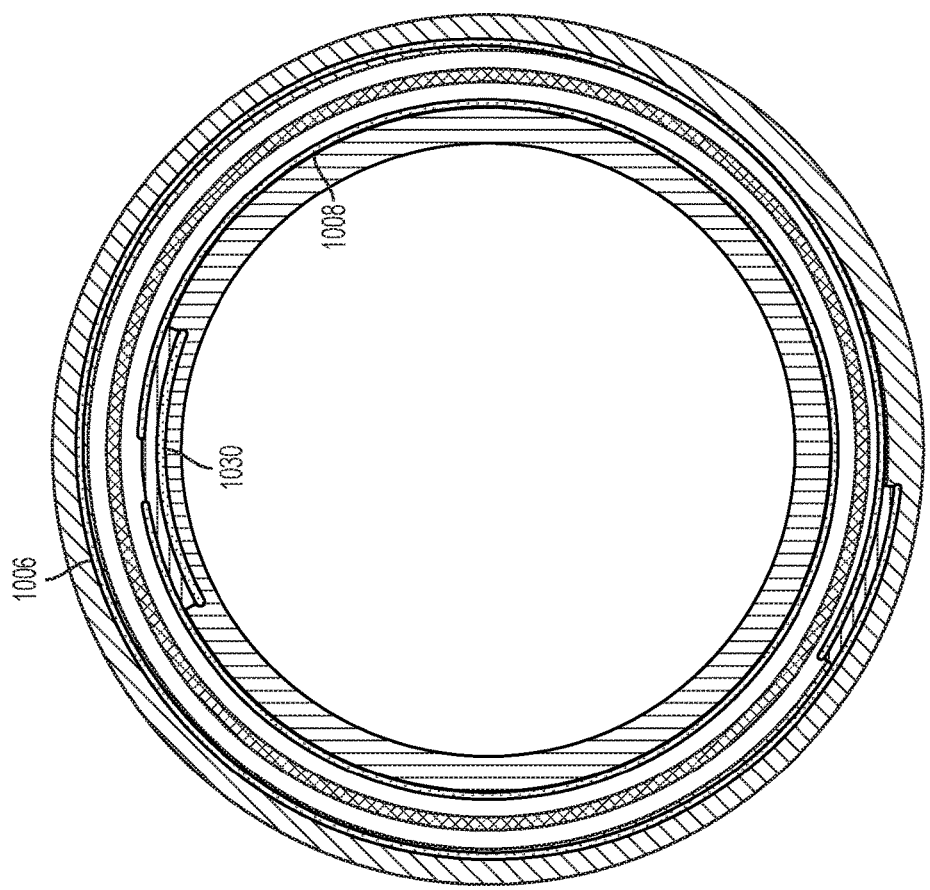
Figure 15C:
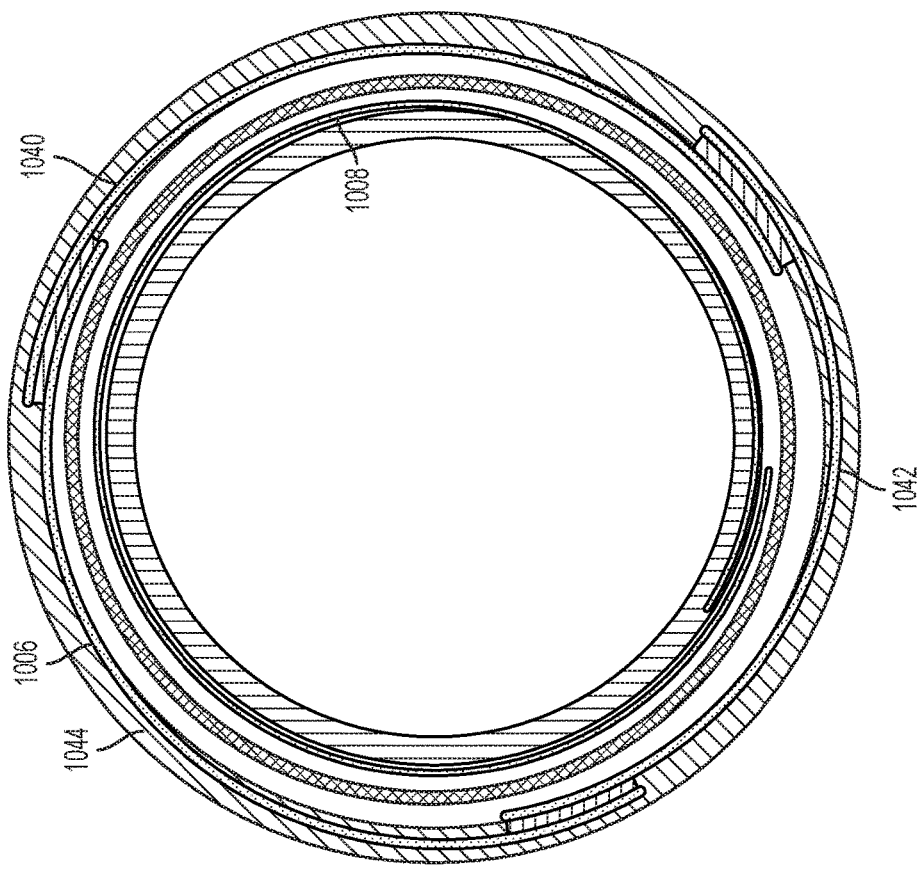

FIGS. 15a-15c illustrate alternate configurations of the RF shielding elements. In FIG. 15a, the RF shielding layers 1006, 1008 include cover portions 1030, 1032. With the water-proof and electrically insulating adhesive, the cover portions 1030, 1032 cover the gaps needed to prevent the RF shielding layers 1006, 1008 from contacting themselves and forming closed loops. The cover portions 1030, 1032 can be formed of the same materials as the RF shielding layers

1006, 1008. As shown in FIG. 15*b*, a "mixed shielding" approach may be used in which one of the RF shielding layers (e.g., shielding layer 1006) is secured to itself (using the water-proof, electrically insulating adhesive) while the other RF shielding layer (e.g., shielding layer 1008) uses a cover portion (e.g., cover portion 1030). As shown in FIG. 15*c*, an RF shielding layer 1006 may be formed by multiple partial rolls (e.g., partial rolls 1040, 1042, 1044) that partially overlap and are secured using water-proof, electrically insulating adhesive.

Figure 16C:
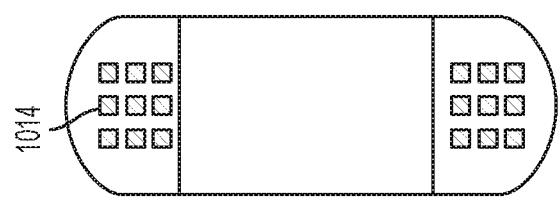
FIGS. 16a-16c illustrate a cut away view from a longitudinal perspective of exemplary pressure sensors with different coil member configurations, according to embodiments of the present disclosure.
Figure 16B:
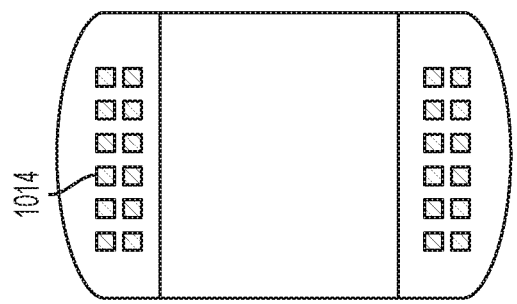
Figure 16A:
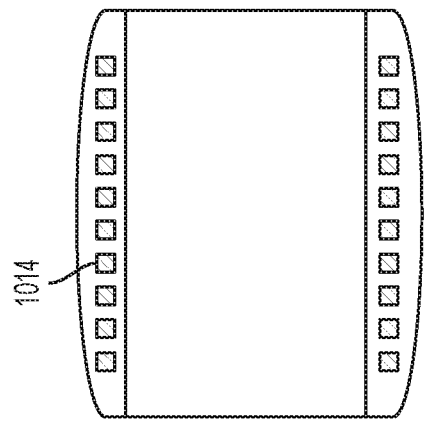

FIGS. 16*a*-16*c* illustrate aspects of the coil configuration according to some embodiments. The coil 1014 can form a single layer (FIG. 16*a*), two layers (FIG. 16*b*), or three layers (FIG. 16*c*). With the same number of total turns, a multi-layered coil may have a slightly higher inductance than a single-layered coil, but this difference is not significant. The choice of a single-layer or multi-layers depends on the specific dimensional requirements for an application. A single-layered coil may be thinner along its radial direction but longer along its axial direction, and a multi-layered coil may be shorter along its axial direction but thicker along its radial direction.

Figure 17C:
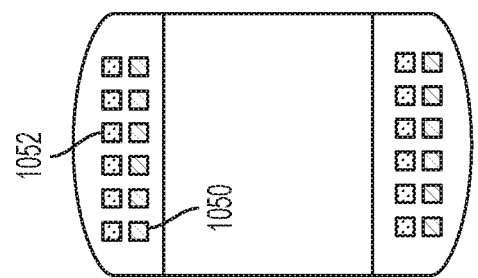
FIGS. 17a-17c illustrate a cut away view from a longitudinal perspective of exemplary pressure sensors with two different coil members and different coil member configurations, according to embodiments of the present disclosure.
Figure 17B:
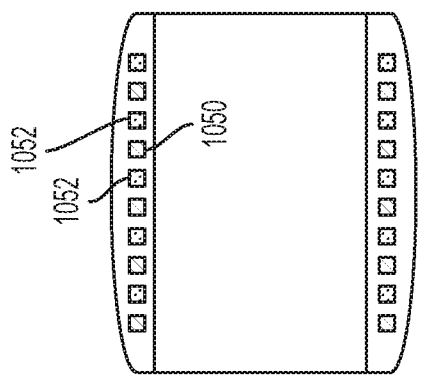
Figure 17A:
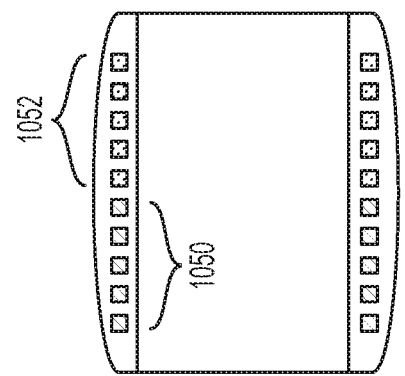
Figure 18C:
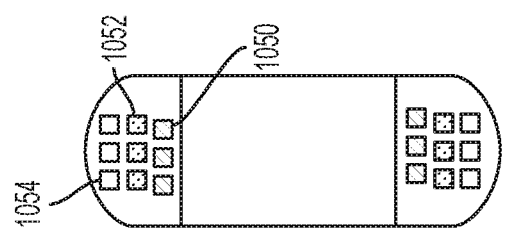
FIGS. 18a-18c illustrate a cut away view from a longitudinal perspective of exemplary pressure sensors with three different coil members and different coil member configurations, according to embodiments of the present disclosure.

FIGS. 17*a*-18*c* illustrate additional aspects of the coil configurations of the present disclosure. As shown in FIGS. 17*a*-17*c* and 18*a*-18*c*, two or three coils (e.g., coils 1050, 1052, 1054) may be used in a side-by-side configuration (FIGS. 17*a* and 18*a*), an interleaved configuration (FIGS. 17*b* and 18*b*), or an overlaid configuration (FIGS. 17*c* and 18*c*). The use of these different configurations can manipulate the LC circuit's resonant frequency, resonance quality factor and/or signal power level.

The amount of power delivered into an LC circuit with an RF shielding configuration, according to some embodiments, is related to the coil's turn number, as more turns result in more power delivered into the circuit. With a large number of turns, a continuous coil may have a high inductance but also exhibits a high resistance loss (due to the coil's long length) and a high capacitance for the LC circuit (due to increased distributed capacitance, e.g., between the coil's adjacent turns and between the coil turns and RF shielding layers 1006, 1008). High capacitance reduces the resonant frequency of the LC circuit, and this reduction is not favorable in some cases. Moreover, high resistance loss and high capacitance significantly reduces the quality factor of the LC circuit, which impedes the resonant frequency measurement and reduces measurement accuracy. Therefore, to have a good Q, in some situations a continuous single coil may require a large-diameter wire (e.g., >100 micrometers in diameter) to reduce resistance loss, which may add to the thickness of the coil as well as the LC sensor's overall size.

The use of multiple short-coils, as discussed with respect to certain embodiments of the present disclosure, addresses these issues. For example, and as shown in FIG. 17*a*, a long continuous coil may be broken into two short coils 1052 that are not electrically connected. Since these two short coils are inductively fully-coupled, the equivalent inductance of two coils in series is similar to the original continuous coil's inductance. However, each short coil may have a smaller distributed capacitance because of the reduced number of turns. Furthermore, because these two short coils are capacitively coupled in series, the equivalent capacitance of two coils together is significantly reduced compared to the original continuous coil's capacitance. As a result, a sensor with multiple short-coils provides a higher resonant frequency and a higher quality factor compared to the sensor with a long single coil with the same number of turns.

Figure 19A:
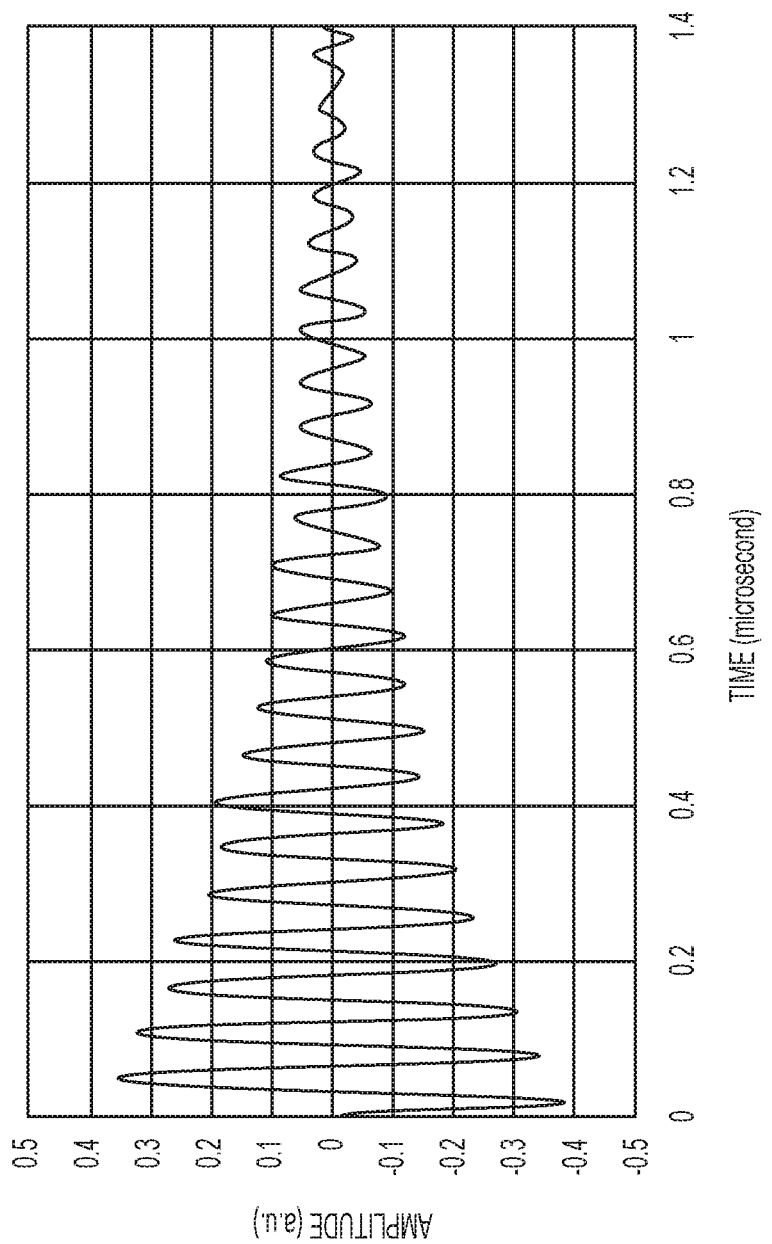
FIGS. 19a-19c show ring-down signals of exemplary LC sensors, comparing single coil and multiple short-coils, according to embodiments of the present disclosure.
Figure 19B:
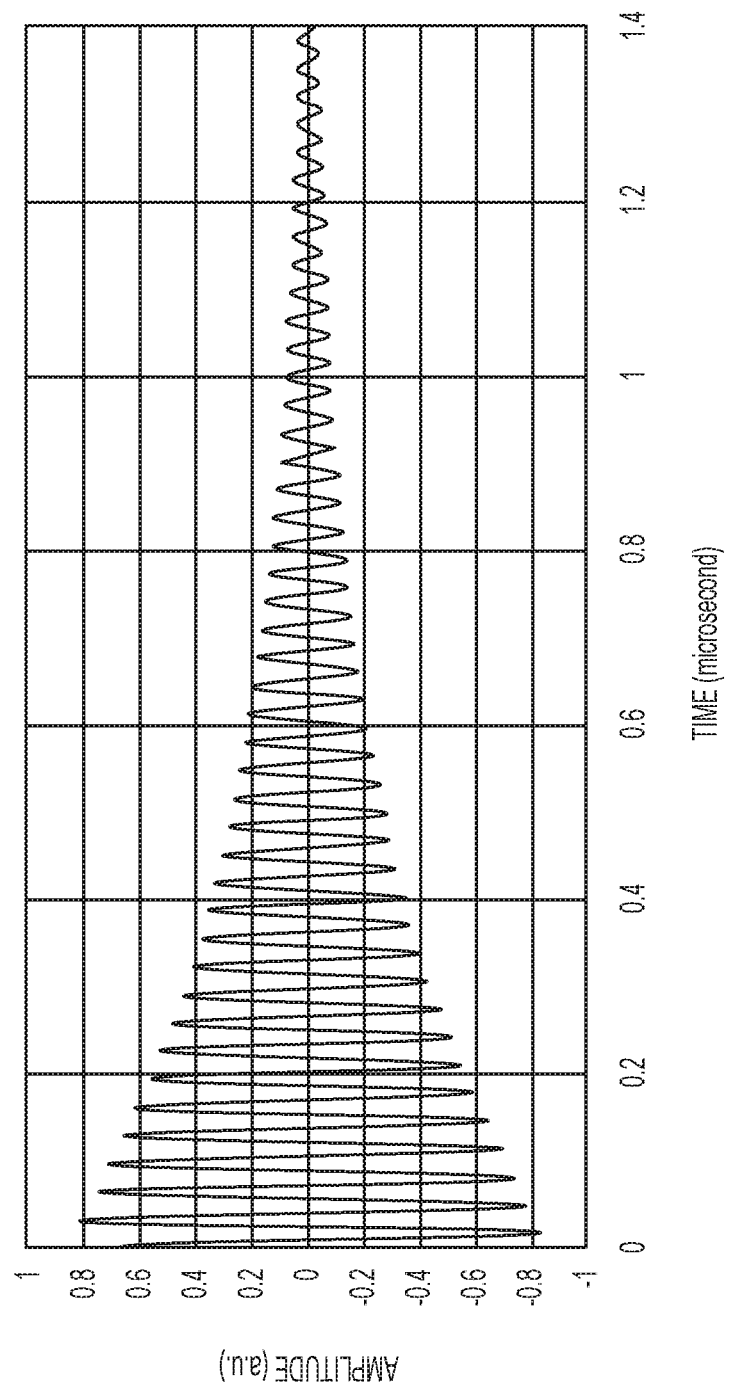

FIG. 19*a* shows a measurement of a ring-down signal of one exemplary LC sensor with a 20-turn coil, while FIG. 19*b* shows a measurement of a ring-down signal of another exemplary LC sensor with two 10-turn short coils in series, in which the coil diameter is about 20 mm and the coil wire diameter is 4 mil (e.g., 100 micrometer). Taking Fourier transforms of these two ring-down signals identifies the resonant frequencies of the LC circuits. In the example shown in FIG. 19*a*, the resonance has a frequency of 16.7 MHz, a quality factor of 23, and a signal amplitude of about 0.4 volts; while in the example shown in FIG. 19*b*, the resonance has a frequency of 30.9 MHz, a quality factor of 41, and a signal amplitude of 0.8 volts. The two-coil sensor (FIG. 19*a*) has almost doubled its frequency, quality factor and power level, compared to the single-coil sensor (FIG. 19*b*).

Figure 19C:
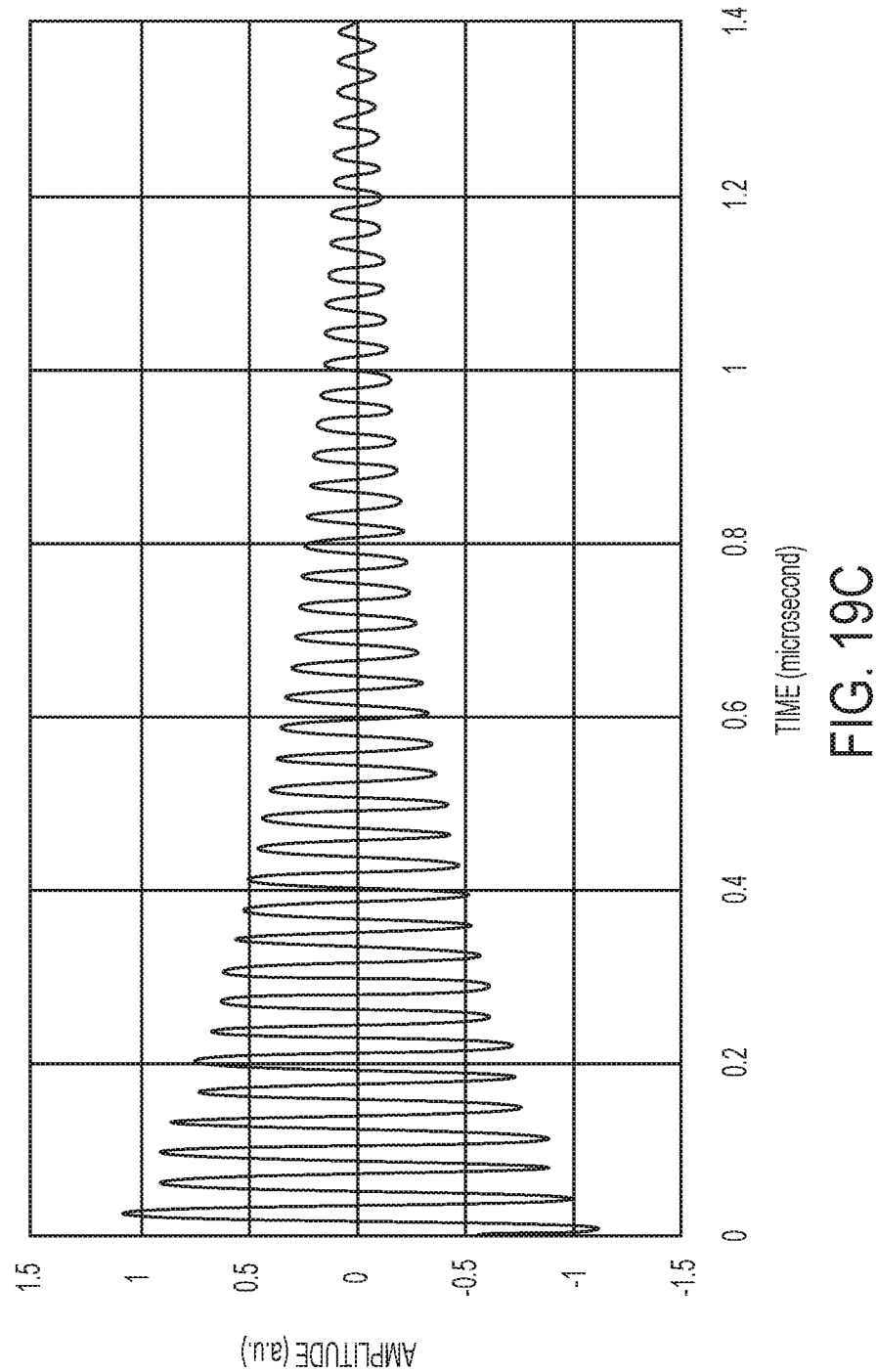

Further, the use of more short-coils can allow the delivery of more power into the LC circuit, assuming each short coil has the same number of turns. FIG. 19*c* shows a measurement of a ring-down signal of another exemplary LC sensor with three 10-turn coils in series, in which the coil diameter is about 20 mm and the coil wire diameter is 4 mil (e.g., 100 micrometers). The sensor with three coils has a resonant frequency of 28.5 MHz, a quality factor of 50, and a signal amplitude of about 1.1 volts. Compared to the double-coil sensor (FIG. 19*b*), the three-coil sensor (FIG. 19*c*) has an increased quality factor, an increased power level, and a slightly decreased frequency.

Figure 18B:
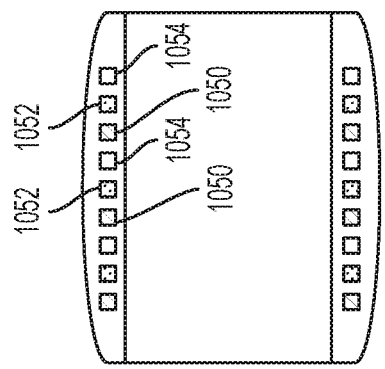
Figure 18A:
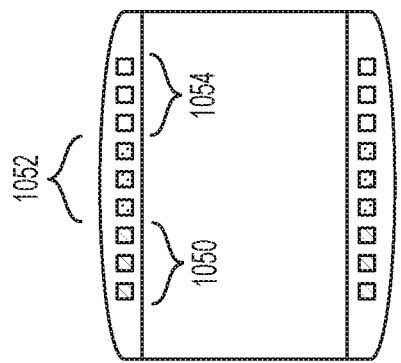
Figure 20:
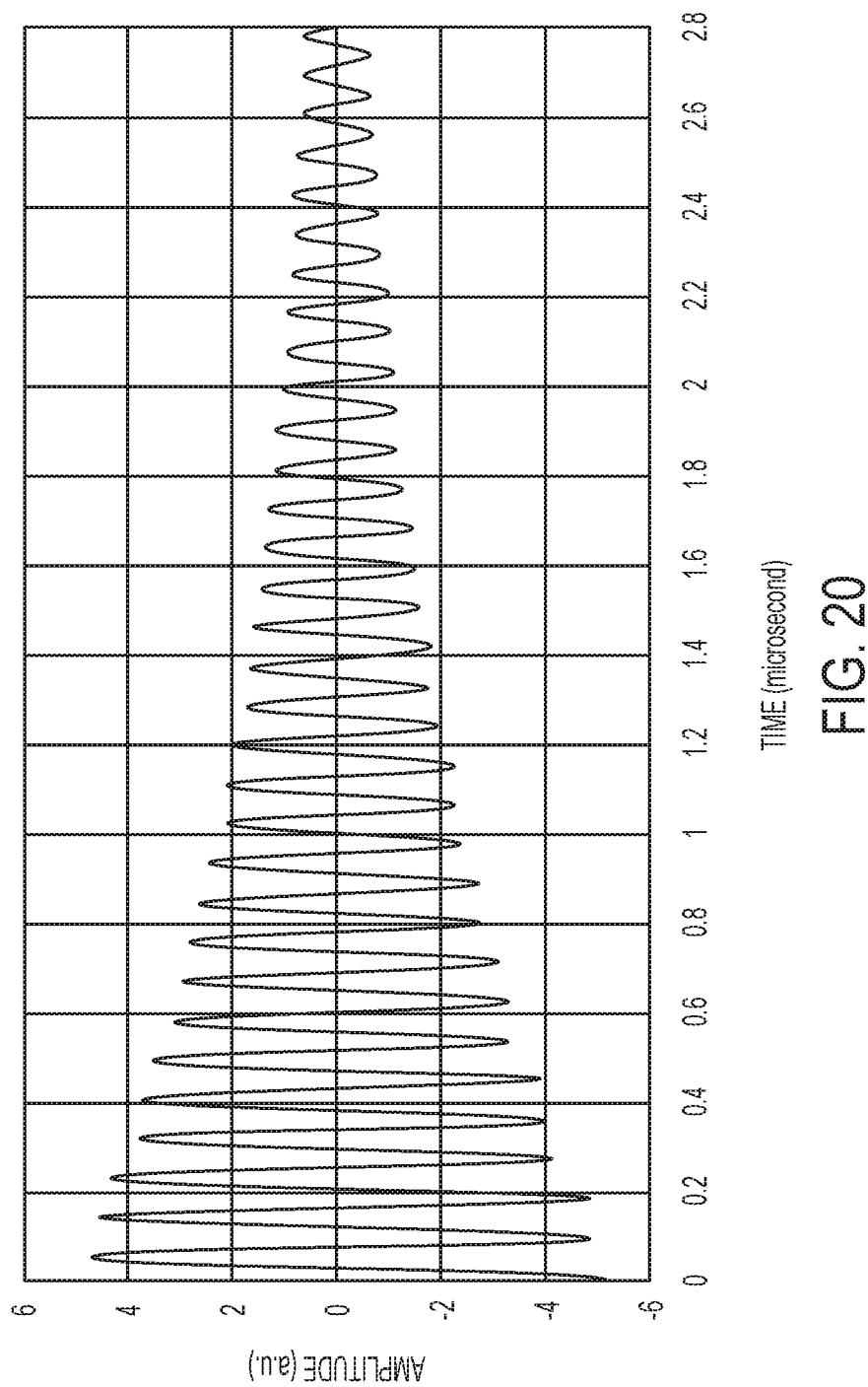
FIG. 20 shows a ring-down signal of an exemplary LC sensor with a large number of small-diameter-wire short-coils, according to embodiments of the present disclosure.

The use of more short-coils in series, either in parallel as shown in FIGS. 17*a* and 18*a* or in interleaved as shown in FIGS. 17*b* and 18*b*, may increase the length of the sensor along its axial direction, but the power level is significantly increased. There are two major sources of energy loss: one is the wire resistance loss, and the other is RF absorption by dielectric media between the wires and RF shielding layers. If smaller diameter wires are used to build short coils, the thickness of the sensor along its radial direction can be further reduced for flexibility, at the expense of increased power loss. However, the increased power loss can be compensated since the larger number of short coils may store more energy than what is lost. FIG. 20 shows a measurement of a ring-down signal of an exemplary LC sensor with sixty-four 10-turn short coils in the interleaved configuration, in which the wire diameter is 25 micrometers and the coil diameter is 25 mm. The sensor has a frequency of 11.4 MHz, a quality factor of 45, and a signal amplitude of about 5 volts. Although made with a small-diameter wire, which has higher electrical resistance than a large-diameter wire, this sensor (FIG. 20) still has a much higher power level compared to the other sensors with a fewer coils (FIG. 19*b* or 19*c*).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. An apparatus comprising:
  a first coaxial RF shielding member and a second coaxial RF shielding member arranged to form a coaxial RF shielding structure, wherein said first coaxial RF shielding member and said second coaxial RF shielding member are partially enclosed shells with only two opposite opens, said first coaxial RF shielding member and said second coaxial RF shielding member are electrically open, and said first coaxial RF shielding member and said second coaxial RF shielding member are spaced from one another by at least one distance and arranged such that said second coaxial RF shielding member is at least partially inside said first coaxial RF shielding member; and one or more electrically conductive coaxial coils provided between said first coaxial RF shielding member and said second coaxial RF shielding member.

2. The apparatus of claim 1, wherein said coaxial RF shielding structure and said one or more electrically conductive coaxial coils form an inductive-capacitive (LC) resonator.

3. The apparatus of claim 2, wherein said LC resonator is adapted to have a resonant frequency within a range from 1 MHz to 50 MHz.

4. The apparatus of claim 1, wherein said first and second coaxial RF shielding members are right or oblique cylindrical shells.

5. The apparatus of claim 1, wherein said first and second coaxial RF shielding members are right or oblique cuboid shells.

6. The apparatus of claim 1, wherein said first coaxial RF shielding member is a continuous hollow roll of conductive film.

7. The apparatus of claim 6, wherein said continuous hollow roll of conductive film is covered with electrical insulation material.

8. The apparatus of claim 7, wherein said electrical insulation material has low water permeability.

9. The apparatus of claim 6, wherein said continuous hollow roll of conductive film has ends that are not electrically connected.

10. The apparatus of claim 1, wherein said first coaxial RF shielding member is an overlapping of multiple short hollow rolls of conductive films.

11. The apparatus of claim 10, wherein said multiple short hollow rolls of conductive films are covered with electrical insulation material.

12. The apparatus of claim 11, wherein said electrical insulation material has low water permeability.

13. The apparatus of claim 10, wherein said multiple short hollow rolls of conductive films have ends that are not electrically connected.

14. The apparatus of claim 1, wherein said one or more electrically conductive coaxial coils is a single layer helix coil.

15. The apparatus of claim 1, wherein said one or more electrically conductive coaxial coils is a double-layer helix coil.

16. The apparatus of claim 1, wherein said one or more electrically conductive coaxial coils is a multiple-layer helix coil.

17. The apparatus of claim 1, wherein said one or more electrically conductive coaxial coils is covered with electrical insulation.

18. The apparatus of claim 17, wherein said electrical insulation is expanded polytetrafluoroethylene (ePTFE).

19. The apparatus of claim 1, further comprising a water-barrier protection cover around said RF shielding structure.

20. The apparatus of claim 1, further comprising a sensing element between said first coaxial RF shielding member and said second coaxial RF shielding member such that said sensing element, said shielding structure, and said one or more electrically conductive coaxial coils form a wireless LC sensor.

21. The apparatus of claim 20, wherein said sensing element is an elastomeric dielectric structure such that said wireless LC sensor is a wireless LC pressure sensor.

22. The apparatus of claim 21, wherein said wireless LC pressure sensor is configured to exhibit a resonant frequency that is based upon a status of said elastomeric dielectric structure.

23. The apparatus of claim 21, wherein said elastomeric dielectric structure is configured to exhibit a changed dielectric characteristic in response to applied pressure.

24. The apparatus of claim 21, wherein said wireless LC pressure sensor is configured to exhibit a resonant frequency that varies in response to changes in the elastomeric dielectric structure due to applied pressure.

25. The apparatus of claim 21, wherein said elastomeric dielectric structure is a compressible dielectric structure.

26. The apparatus of claim 21, wherein said elastomeric dielectric structure is a cavity in a hermetic seal.

27. The apparatus of claim 21, wherein said elastomeric dielectric structure is porous in a hermetic seal.

28. The apparatus of claim 21, wherein said elastomeric dielectric structure is a distribution of elastic solids.

29. The apparatus of claim 28, wherein said elastic solids are selected from a group consisting essentially of balls, rods, pyramids, and trapezoid-prisms.

30. The apparatus of claim 20, wherein said sensing element is a temperature-sensitive dielectric such that said wireless LC sensor is a wireless LC temperature sensor.

31. The apparatus of claim 30, wherein said wireless LC temperature sensor is configured to exhibit a resonant frequency that is based upon a status of said temperature-sensitive dielectric.

32. The apparatus of claim 30, wherein said temperature-sensitive dielectric is configured to exhibit a changed dielectric characteristic in response to environmental temperature changes.

33. The apparatus of claim 30, wherein said wireless LC temperature sensor is configured to exhibit a resonant frequency that varies in response to changes in the temperature-sensitive dielectric due to environmental temperature changes.

34. The apparatus of claim 20, wherein said wireless LC sensor further comprises a crushable and expandable frame to form a crushable LC sensor.

35. The apparatus of claim 34, wherein said crushable LC sensor has a thickness of about 0.1 mm to 1 mm.

36. The apparatus of claim 34, wherein said crushable and expandable frame is configured so that said crushable LC sensor folds up into a compact form and then expands post-delivery.

37. The apparatus of claim 36, wherein said crushable LC sensor is configured to engage a rolling supporter as it folds up.

38. The apparatus of claim 37, wherein said rolling supporter is selected from a group consisting essentially of expanded polytetrafluoroethylene (ePTFE) rods or films.

39. The apparatus of claim 1, further comprising a flexible but non-compressible dielectric between said first RF shielding member and said second RF shielding member such that said coaxial RF shielding structure and said one or more electrically conductive coaxial coils form a wireless LC sensor for sensing diameter or size.

40. The apparatus of claim 39, wherein said wireless LC sensor is configured to exhibit a resonant frequency that is based upon a diameter or size of said wireless LC sensor.

41. The apparatus of claim 39, wherein said wireless LC sensor is configured to exhibit a resonant frequency that varies in response to a change in a diameter or size of said wireless LC sensor.

42. The apparatus of claim 1, further comprising a MEMS sensor with an ASIC between said first RF shielding member and said second RF shielding member such that said one or more electrically conductive coaxial coils is configured as a transceiver antenna of said MEMS sensor.

43. The apparatus of claim 42, wherein said one or more electrically conductive coaxial coils is configured to receive externally delivered RF energy.

44. The apparatus of claim 42, wherein said one or more electrically conductive coaxial coils are configured to receive externally delivered RF energy and supply that energy to said MEMS sensor.

45. The apparatus of claim 42, further comprising a water barrier cover.

46. A method of measuring flow in a graft, comprising:
imbedding a first passive LC pressure sensor in a middle portion of a narrowed section of said graft, wherein said first passive LC pressure sensor is configured to produce a first signal that is a function of liquid pressure within said graft;
imbedding a second passive LC pressure sensor at an end of said narrowed section, wherein said second passive LC pressure sensor is configured to produce a second signal that is a function of liquid pressure within said graft; and
collecting and analyzing said first signal and said second signal to determine the flow through said graft.

47. A method of introducing a passive LC sensor lying on an outer surface of a treatment stent-graft into a vascular lumen, comprising the steps of:
introducing a self-expanding passive LC sensor in a folded configuration to a selected site in a vascular lumen;
releasing the self-expanding passive LC sensor to allow the self-expanding passive LC sensor to expand from its folded configuration at the selected site in said vascular lumen;
passing a self-expanding treatment stent-graft in a folded configuration through the expanded passive LC sensor at the selected site in said vascular lumen;
adjusting the location of said self-expanding passive LC sensor relative to said self-expanding treatment stent-graft; and
releasing said self-expanding treatment stent-graft to allow the self-expanding treatment stent-graft to expand from its folded configuration at the selected site in said vascular lumen with the self-expanding passive LC sensor laying on an outer surface of said self-expanding treatment stent-graft.

48. A method of introducing a passive LC sensor lying against an inner surface of a treatment stent-graft into a lumen, comprising the steps of:
introducing a folded self-expanding stent-graft to a selected site in a vascular lumen;
expanding the self-expanding stent-graft at the selected site in said vascular lumen;
introducing a folded self-expanding LC sensor through a lumen of said expanded stent-graft at the selected site in the vascular lumen; and
expanding the self-expanding LC sensor so that it lays against an inner surface of said expanded stent-graft.

* * * * *